(12) United States Patent
Yaffe et al.

(10) Patent No.: US 12,295,615 B2
(45) Date of Patent: May 13, 2025

(54) SURGICAL LAPAROSCOPIC PORTS FOR IMPLANTING MEDICAL SYSTEMS

(71) Applicant: Verily Life Sciences LLC, South San Francisco, CA (US)

(72) Inventors: Benjamin K. Yaffe, San Francisco, CA (US); Shivkumar Sabesan, San Mateo, CA (US); Eric Irwin, South San Francisco, CA (US)

(73) Assignee: Verily Life Sciences LLC, Dallax, TX (US)

( * ) Notice: Subject to any disclaimer, the term of this patent is extended or adjusted under 35 U.S.C. 154(b) by 650 days.

(21) Appl. No.: 17/325,820

(22) Filed: May 20, 2021

(65) Prior Publication Data
US 2021/0267629 A1 Sep. 2, 2021

Related U.S. Application Data

(63) Continuation of application No. 16/408,123, filed on May 9, 2019, now Pat. No. 11,039,856.
(Continued)

(51) Int. Cl.
*A61B 17/34* (2006.01)
*A61N 1/36* (2006.01)

(52) U.S. Cl.
CPC ...... *A61B 17/3421* (2013.01); *A61B 17/3403* (2013.01); *A61N 1/36062* (2017.08);
(Continued)

(58) Field of Classification Search
CPC ............ A61B 17/3421; A61B 17/3423; A61B 2017/3433; A61B 2017/3445
See application file for complete search history.

(56) References Cited

U.S. PATENT DOCUMENTS

| 4,545,374 A | 10/1985 | Jacobson |
| 5,562,677 A | 10/1996 | Hildwein et al. |

(Continued)

FOREIGN PATENT DOCUMENTS

| AU | 2015201956 | 5/2015 |
| CN | 101466318 A | 6/2009 |

(Continued)

OTHER PUBLICATIONS

"Helios, a CyTOF System", Fluidigm, Products, Available Online at: https://www.fluidigm.com/products/helios#overview, 2015, 5 pages.
(Continued)

*Primary Examiner* — Ellen C Hammond
*Assistant Examiner* — Holly Joanna Lane
(74) *Attorney, Agent, or Firm* — Kilpatrick Townsend & Stockton LLP

(57) ABSTRACT

The present disclosure relates to laparoscopic surgery, and in particular to laparoscopic ports for facilitating the implant of medical systems such as a neuromodulation system into the body of a patient. Particularly, aspects are directed to a cannula assembly having a cannula housing and a cannula sleeve comprising a sleeve body extending from a distal end of the cannula housing. The cannula sleeve has a semi-rectangular cross section including: (i) a rounded rectangular portion configured to accommodate feeding the neuromodulation system through the cannula assembly, and (ii) a circular portion configured to accommodate insertion of the one or more surgical instruments through the cannula assembly.

6 Claims, 16 Drawing Sheets

Related U.S. Application Data

(60) Provisional application No. 62/669,485, filed on May 10, 2018.

(52) U.S. Cl.
CPC ............ *A61B 2017/3433* (2013.01); *A61B 2017/3443* (2013.01); *A61B 2017/3445* (2013.01); *A61N 1/36067* (2013.01)

(56) References Cited

U.S. PATENT DOCUMENTS

| | | | |
|---|---|---|---|
| 5,762,629 | A | 6/1998 | Kambin |
| 9,532,885 | B2 | 1/2017 | Lauryssen et al. |
| 9,867,605 | B2* | 1/2018 | Adams .............. A61B 17/0218 |
| 10,809,266 | B2 | 10/2020 | Peikon et al. |
| 11,039,856 | B2* | 6/2021 | Yaffe .................. A61N 1/36062 |
| 2002/0016607 | A1* | 2/2002 | Bonadio ............ A61M 25/0119 |
| | | | 606/192 |
| 2007/0003950 | A1 | 1/2007 | Shen et al. |
| 2007/0088277 | A1 | 4/2007 | Mcginley et al. |
| 2010/0081988 | A1 | 4/2010 | Kahle et al. |
| 2010/0152747 | A1 | 6/2010 | Decre et al. |
| 2010/0209454 | A1 | 8/2010 | Wimmer et al. |
| 2011/0144619 | A1 | 6/2011 | Meng et al. |
| 2011/0152626 | A1 | 6/2011 | Smith |
| 2013/0218188 | A1* | 8/2013 | McFarlane ......... A61B 17/3423 |
| | | | 606/185 |
| 2013/0310773 | A1 | 11/2013 | Richard et al. |
| 2014/0256588 | A1 | 9/2014 | Glezer et al. |
| 2015/0100244 | A1 | 4/2015 | Hannum |
| 2015/0182233 | A1 | 7/2015 | Van Wyk et al. |
| 2015/0376609 | A1 | 12/2015 | Hindson et al. |
| 2016/0051243 | A1* | 2/2016 | Heiges ............... A61B 17/3439 |
| | | | 600/204 |
| 2016/0115474 | A1 | 4/2016 | Jelinek et al. |
| 2016/0310725 | A1* | 10/2016 | De La Rama ..... A61B 17/3468 |
| 2018/0024139 | A1 | 1/2018 | Peikon et al. |
| 2018/0044731 | A1 | 2/2018 | Valouev et al. |
| 2018/0320241 | A1 | 11/2018 | Nolan |
| 2019/0025299 | A1 | 1/2019 | Vigneault et al. |
| 2019/0216498 | A1 | 7/2019 | Maddur et al. |

FOREIGN PATENT DOCUMENTS

| | | |
|---|---|---|
| CN | 103945895 A | 7/2014 |
| EP | 1189652 | 3/2002 |
| WO | 0074760 A2 | 12/2000 |
| WO | 2016100976 | 6/2016 |
| WO | 2017075294 A1 | 5/2017 |
| WO | 2018017949 | 1/2018 |

OTHER PUBLICATIONS

"Intracellular FLow Cytometry", BD Biosciences, 2012, 16 pages.
U.S. Appl. No. 15/656,423, Final Office Action, Mailed On Jan. 27, 2020, 9 pages.
U.S. Appl. No. 15/656,423, Non-Final Office Action, Mailed On Jul. 31, 2019, 10 pages.
U.S. Appl. No. 15/656,423, Notice of Allowance, Mailed On Jun. 8, 2020, 8 pages.
U.S. Appl. No. 16/408,123, Final Office Action, Mailed On Dec. 3, 2020, 7 pages.
U.S. Appl. No. 16/408,123, Non-Final Office Action, Mailed On Aug. 18, 2020, 7 pages.
U.S. Appl. No. 16/408,123, Notice of Allowance, Mailed On Feb. 22, 2021, 6 pages.
Ahram et al., "Estimation of Membrane Proteins in the Human Proteome", In Silico Biology, vol. 6, No. 5, IOS Press, 2006, pp. 379-386.
Alves et al., "Conjugation of a Reactive Thiol at the Nucleotide Binding Site for Site-Specific Antibody Functionalization", Bioconjugate Chemistry, vol. 25, No. 7, 2014, pp. 1198-1202.
Duban-Deweer et al., "Proteomic Analysis of Plasma Membrane Proteins in an In Vitro Blood-Brain Barrier Model", Proteomics—Human Diseases and Protein Functions, Feb. 10, 2012, pp. 397-398.
Application No. EP17748996.0, Office Action, Mailed On Sep. 10, 2020, 6 pages.
Gaur, "Prokaryotic and eukaryotic non-membrane proteins have biased amino acid distribution", Journal of Computer Science and Systems Biology, vol. 2, No. 6, Nov.-Dec. 2009, pp. 298-299.
Green, "Advances in Protein Chemistry", Avidin, vol. 29, 1975, pp. 85-133.
Maier et al., "Correlation of mRNA and Protein in Complex Biological Samples", FEBS Letters, vol. 583, No. 24, 2009, pp. 3966-3973.
Ong et al., "Stable Isotope Labeling by Amino Acids in Cell Culture, Silac, as a Simple and Accurate Approach to Expression Proteomics", Molecular & Cellular Proteomics, vol. 1, No. 5, 2002, pp. 376-386.
Application No. PCT/US2017/043273, International Preliminary Report on Patentability, Mailed On Jan. 31, 2019, 8 pages.
PCT/US2017/043273, "PCT Search Report", Nov. 3, 2017, 14 pages.
Application No. PCT/US2019/031789, International Preliminary Report on Patentability, Mailed On Nov. 19, 2020, 9 pages.
Application No. PCT/US2019/031789, International Search Report and Written Opinion, Mailed On Aug. 26, 2019, 15 pages.
Shibao et al., "A newly developed oval-shaped port device (E•Z Access Oval type) for use in reduced port surgery: initial clinical experiences with cholecystectomy", Surgical Technology International, vol. 23, Sep. 2013, pp. 75-79.
Wertz et al., "Influence of Water on Protein Structure. An Analysis of the Preferences of Amino Acid Residues for the Inside or Outside and for Specific Conformations in a Protein Molecule", Macromolecules, vol. 11, No. 1, 1978, pp. 9-15.
Application No. EP17748996.0, Office Action, Mailed On Aug. 17, 2022, 5 pages.
U.S. Appl. No. 17/074,224, "Non-Final Office Action", May 5, 2023, 13 pages.
EP19725631.6, "Intention to Grant", Feb. 23, 2023, 9 pages.
Application No. CN201980031535.6, Office Action, Mailed On Apr. 8, 2024, 6 pages.
Application No. EP17748996.0, Office Action, Mailed On Apr. 24, 2024, 4 pages.
U.S. Appl. No. 17/074,224, Non-Final Office Action, Mailed On Oct. 23, 2023, 12 pages.
Application No. CN201980031535.6, Office Action, Mailed On Sep. 28, 2023, 9 pages.
Application No. CN201980031535.6, Office Action, Mailed On Jun. 21, 2024, 6 pages.

\* cited by examiner

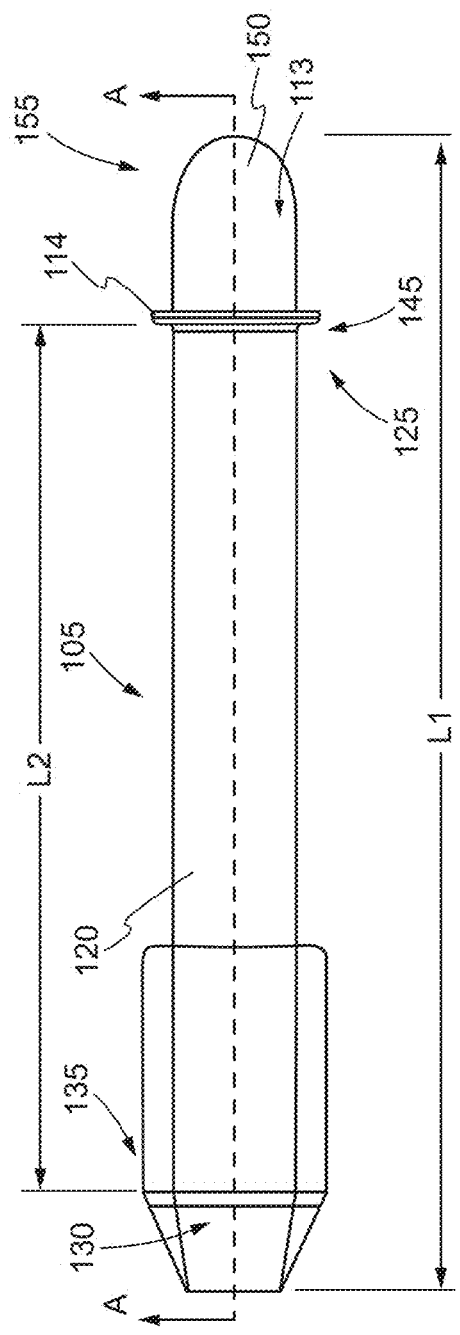
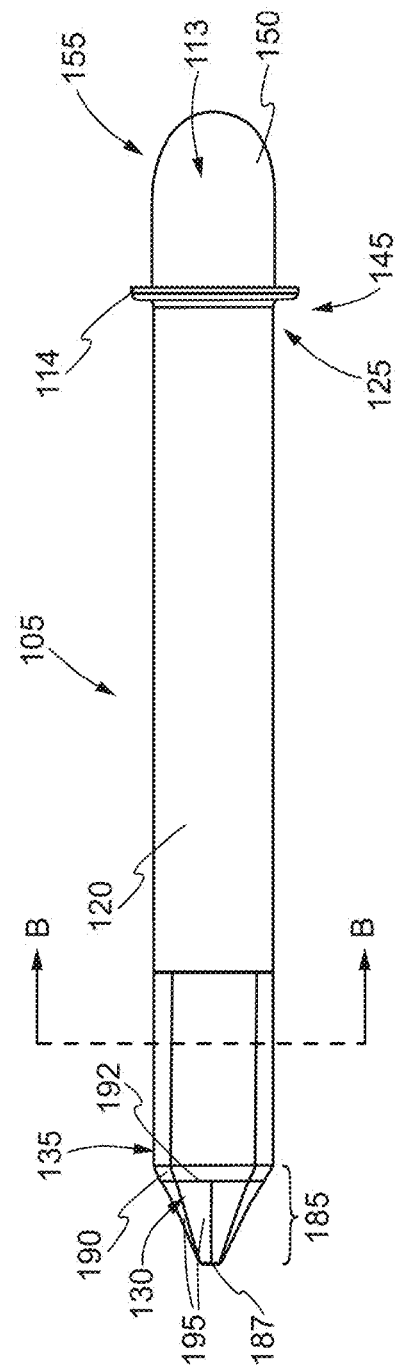
FIG. 1D
FIG. 1E

SECTION A-A

SECTION B-B

SURGICAL LAPAROSCOPIC PORTS FOR IMPLANTING MEDICAL SYSTEMS

CROSS-REFERENCE TO RELATED APPLICATION

This application is a continuation of U.S. patent application Ser. No. 16/408,123, filed on May 9, 2019, which claims priority and benefit to U.S. Provisional Application No. 62/669,485, filed on May 10, 2018, both of which are incorporated herein by reference in their entireties.

FIELD OF THE INVENTION

The present disclosure relates to laparoscopic surgery, and in particular to laparoscopic ports for facilitating the implant of medical systems such as a neuromodulation system into the body of a patient.

BACKGROUND

Normal neural activity is an intricate balance of electrical and chemical signals which can be disrupted by a variety of insults (genetic, chemical or physical trauma) to the nervous system, causing cognitive, motor and sensory impairments. Similar to the way a cardiac pacemaker or defibrillator corrects heartbeat abnormalities, neuromodulation therapies help to reestablish normal neural balance. In particular instances, neuromodulation therapies utilize medical device technologies to enhance or suppress activity of the nervous system for the treatment of disease. These technologies include implantable as well as non-implantable neuromodulation devices and systems that deliver electrical, chemical or other agents to reversibly modify brain and nerve cell activity. The most common neuromodulation therapy is spinal cord stimulation to treat chronic neuropathic pain. In addition to chronic pain relief, some examples of neuromodulation therapies include deep brain stimulation for essential tremor, Parkinson's disease, dystonia, epilepsy and psychiatric disorders such as depression, obsessive compulsive disorder and Tourette syndrome; sacral nerve stimulation for pelvic disorders and incontinence; vagus nerve stimulation for rheumatoid arthritis; gastric and colonic stimulation for gastrointestinal disorders such as dysmotility or obesity; vagus nerve stimulation for epilepsy, obesity or depression; carotid artery stimulation for hypertension, and spinal cord stimulation for ischemic disorders such as angina and peripheral vascular disease.

Rheumatoid arthritis is an autoimmune disorder that occurs when the immune system mistakenly attacks body's own tissues. Unlike the wear and tear damage (due to age and/or extreme sports) of osteoarthritis, rheumatoid arthritis affects the lining of the joints, causing a painful swelling that can eventually result in bone erosion and joint deformity. The inflammation associated with rheumatoid arthritis is what can damage other parts of the body as well. While new types of medications have improved treatment options dramatically, severe rheumatoid arthritis can still cause physical disabilities. Recently, neuromodulation has been suggested as a potential treatment option for patients suffering from rheumatoid arthritis. Specifically, electrical stimulation of the splenic plexus has shown promise. However, since patients with rheumatoid arthritis may already be in a pro inflamed state, it is important that device implantation be performed with minimal invasiveness. From this perspective, implantable neuromodulation devices that are designed to be deliverable to an anatomical target such as the splenic plexus using minimally invasive surgery may have a higher probability of reducing the potential for complications in a patient population that is already in an inflamed state.

Laparoscopic surgery also referred to as minimally invasive surgery describes the performance of surgical procedures with the assistance of a video camera and several thin instruments. During the surgical procedures, small incisions of up to half an inch are made in the body of a patient and tubes called ports are placed through these incisions, which provide access to an inside cavity of the patient. The laparoscopic ports typically function as a portal for the subsequent placement of instruments, such as laparoscopes, graspers, scissors, staplers, etc. The laparoscopic ports also function to maintain pressure of insufflation gas in the cavity, which allows for a wider field of view with the cavity and easier manipulation of objects within the cavity. As the incisions used in laparoscopic surgery are much smaller than the incisions used in open surgery and the ports allow for the introduction of items without contacting the bacteria of the skin, laparoscopic surgery is capable of minimizing risk of infection, complications, and post-operative pain. Thus, laparoscopic surgery is one option for the safe and reliable placement of a neural interface, lead, and an implantable pulse generator around neural structures such as the splenic plexus. Laparoscopic surgery is currently used in the practice of medicine, for both diagnostic and therapeutic purposes. For example, the minimally invasive approach has become the method of choice for treating most benign abdominal diseases that require surgery including hernia repairs, gastric bypass, bowel resection, and organ removal. More recently, laparoscopic surgery has also been used in the practice of medicine, for implanting medical systems within a patient such as an adjustable gastric around the stomach.

The conventional laparoscopic ports for the aforementioned laparoscopic procedures may be exemplified as a cannula device or a trocar. Trocars typically comprise an outer housing and seal assembly, a sleeve that fits inside the housing and seal assembly and a piercing stylus (e.g., an obturator) which slots into the sleeve such that the tip of the stylus protrudes from the lower end of the device. The stylus may be used to create an opening in the abdominal wall through which the sleeve is inserted and fixed into place, following which the stylus is removed through an opening in the upper end of the device to allow insertion of a laparoscope or other surgical tools through the sleeve. Where trocar was once used to refer solely to the piercing stylus, the term "trocar" is now generally and herein used to refer to the whole assembly. A wide range of laparoscopic cannula devices and trocars exist having a variety of lengths and diameters. However, the medical systems (e.g., gastric bands) that have been delivered through laparoscopic ports are typically circular and/or flexible and configured to pass through the conventional variety of lengths and diameters for cannula devices and trocars. The need to allow access to new and existing surgical tools for placement of flexible neural interfaces, leads, and a rigid non-circular implantable pulse generator will require the laparoscopic port's outer cannula, inner lumen, seals, and/or incising stylus to be varied in form from the conventional variety of lengths and diameters. Accordingly, the need exists for systems and methods to safely and reliably place neural interfaces, leads, and an implantable pulse generator around neural structures in a body cavity.

BRIEF SUMMARY

In various embodiments, a cannula assembly is provided comprising: a cannula housing comprising a first opening at a proximal end; and a cannula sleeve comprising a sleeve body extending from a distal end of the cannula housing, the sleeve body comprising a distal end having a second opening, a proximal end connected to the cannula housing, and a semi-rectangular cross section extending from the proximal end of the sleeve body to the distal end of the sleeve body. The semi-rectangular cross section comprises: (i) a rounded rectangular portion, and (ii) a circular portion, and the circular portion extends beyond the rounded rectangular portion in a direction parallel to a plane of the semi-rectangular cross section.

In some embodiments, a top region of the circular portion extends above the rounded rectangular portion and a bottom region of the circular portion extends below the rounded rectangular portion.

In some embodiments, a top region of the circular portion extends beyond the rounded rectangular portion in a first direction parallel to the plane of the semi-rectangular cross section and a bottom region of the circular portion extends beyond the rounded rectangular portion in a second direction parallel to the plane of the semi-rectangular cross section, and the second direction is opposite from the first direction.

In some embodiments, the top region of the circle portion is defined by at least a first top face and a second top face meeting at a top apex, the bottom region of the circle portion is defined by at least a first bottom face and a second bottom face meeting at a bottom apex, a horizontal region of the rounded rectangular portion is defined by at least a latitudinal width between inner surfaces of a first side face and a second side face, the top apex is disposed above the horizontal region, and the bottom apex is disposed below the horizontal region.

In some embodiments, a tangential angle between tangential segments of each of the first top face, the second top face, the first bottom face, and the second bottom face, and a horizontal mid line of the semi-rectangular cross section is an acute angle.

In some embodiments, a horizontal region of the rounded rectangular portion is defined by at least a longitudinal height that is less than a diameter of the circular portion.

In some embodiments, the semi-rectangular cross section further comprises a curved segment between each of the first top face and the first side face, the first bottom face and the first side face, the second top face and the second side face, and the second bottom face and the second side face.

In various embodiments, a cannula assembly is provided comprising: a cannula housing comprising a first opening at a proximal end; and a cannula sleeve comprising a sleeve body extending from a distal end of the cannula housing, the sleeve body comprising a distal end having a second opening, a proximal end connected to the cannula housing, and a semi-rectangular cross section extending from the proximal end of the sleeve body to the distal end of the sleeve body. The semi-rectangular cross section comprises: (i) a rounded rectangular portion, and (ii) a circular portion. A top region of the circle portion is defined by a first top face and a second top face meeting at a top apex, a bottom region of the circle portion is defined by a first bottom face and a second bottom face meeting at a bottom apex, a horizontal region of the rounded rectangular portion is defined by a latitudinal width between inner surfaces of a first side face and a second side face, and a tangential angle between tangential segments of each of the first top face, the second top face, the first bottom face, and the second bottom face and a horizontal mid line of the semi-rectangular cross section that is greater than 1.0° (for example from 13.0° to 19.6°).

In some embodiments, the latitudinal width is from 15.0 mm to 25.0 mm. Optionally, the semi-rectangular cross section further comprises a longitudinal height between inner surfaces of the top apex and the bottom apex that is from 9.0 mm to 15.0 mm. Optionally, the semi-rectangular cross section further comprises a radius of curvature for the top apex and the bottom apex that is from 5.1 R to 7.7 R. Optionally, the semi-rectangular cross section further comprises a radius of curvature for turns between the first top face and the first side face, the first bottom face and the first side face, the second top face and the second side face, and the second bottom face and the second side face that is from 2.2 R to 3.4 R.

In some embodiments, the cannula sleeve further comprises a hub attached to the proximal end of the sleeve body, the cannula housing comprises a slot that matches a size and shape of the hub, and the hub sits in the slot for connecting the cannula sleeve to the cannula housing. Optionally, the distal end of the cannula housing has a third opening, and the cannula housing further comprises a seal located in an interior region between the first opening and the third opening. Optionally, the first opening and the third opening have a semi-rectangular cross section that is different from the semi-rectangular cross section of the sleeve body.

In some embodiments, the semi-rectangular cross section of the first opening and the third opening comprises: a top arced face having a top apex, a bottom arced face having a bottom apex, a first side face joining the top arced face to the bottom arced face, a second side face joining the top arced face to the bottom arced face, a latitudinal width between inner surfaces of the first side face and the second side face that is from 16.0 mm to 26.0 mm, a longitudinal height between inner surfaces of the top apex and the bottom apex that is from 9.0 mm to 15.0 mm, and a radius of curvature for turns between the top arced face and the first side face, the top bottom face and the first side face, the top arced face and the second side face, and the bottom arced face and the second side face that is from 2.2 R to 3.4 R.

In various embodiments, a cannula assembly is provided comprising: a cannula housing comprising a distal end, a proximal end having a first opening, and an interior region between the distal end and the proximal end; and a cannula sleeve comprising a sleeve body extending from the distal end of the cannula housing, the sleeve body comprising a distal end having a second opening, a proximal end connected to the interior region of the cannula housing, and a semi-rectangular cross section extending from the proximal end of the sleeve body to the distal end of the sleeve body. The semi-rectangular cross section comprises: a first top face and a second top face meeting at a top apex, a first bottom face and a second bottom face meeting at a bottom apex, a first side face joining the first top face to the first bottom face, a second side face joining the second top face to the second bottom face, a latitudinal width between inner surfaces of the first side face and the second side face that is from 15.0 mm to 25.0 mm, a longitudinal height between inner surfaces of the top apex and the bottom apex that is from 9.0 mm to 15.0 mm, and a tangential angle between tangential segments of each of the first top face, the second top face, the first bottom face, and the second bottom face and a horizontal mid line of the semi-rectangular cross section that is from 13.0° to 19.6°.

In some embodiments, the semi-rectangular cross section further comprises a radius of curvature for the top apex and the bottom apex that is from 5.1 R to 7.7 R. Optionally, the semi-rectangular cross section further comprises a radius of curvature for turns between the first top face and the first side face, the first bottom face and the first side face, the second top face and the second side face, and the second bottom face and the second side face that is from 2.2 R to 3.4 R. Optionally, the cannula sleeve further comprises a hub attached to the proximal end of the sleeve body, the cannula housing comprises a slot that matches a size and shape of the hub, and the hub sits in the slot for connecting the cannula sleeve to the cannula housing. Optionally, the distal end of the cannula housing has a third opening, and the cannula housing further comprises a seal located in the interior region between the first opening and the third opening. Optionally, the first opening and the third opening have a semi-rectangular cross section.

In some embodiments, the semi-rectangular cross section of the first opening and the third opening comprises: a top arced face having a top apex, a bottom arced face having a bottom apex, a first side face joining the top arced face to the bottom arced face, a second side face joining the top arced face to the bottom arced face, a latitudinal width between inner surfaces of the first side face and the second side face that is from 16.0 mm to 26.0 mm, a longitudinal height between inner surfaces of the top apex and the bottom apex that is from 9.0 mm to 15.0 mm, and a radius of curvature for turns between the top arced face and the first side face, the top bottom face and the first side face, the top arced face and the second side face, and the bottom arced face and the second side face that is from 2.2 R to 3.4 R.

In various embodiments, a trocar assembly is provided comprising: an obturator assembly comprising: an obturator housing; an obturator tip; and an obturator body extending from a distal end of the obturator housing to the obturator tip, the obturator body comprising a first semi-rectangular cross section extending from the obturator housing to the obturator tip. The trocar assembly further comprises a cannula assembly comprising: a cannula housing; and a cannula sleeve comprising a sleeve body extending from a distal end of the cannula housing, the sleeve body comprising a second semi-rectangular cross section that is offset from the first semi-rectangular cross section to accommodate insertion of the obturator body within the cannula sleeve. The second semi-rectangular cross section comprises: (i) a rounded rectangular portion, and (ii) a circular portion, and the circular portion extends beyond the rounded rectangular portion in a direction parallel to a plane of the second semi-rectangular cross section.

In some embodiments, a top region of the circular portion extends above the rounded rectangular portion and a bottom region of the circular portion extends below the rounded rectangular portion.

In some embodiments, a top region of the circular portion extends beyond the rounded rectangular portion in a first direction parallel to the plane of the second semi-rectangular cross section, a bottom region of the circular portion extends beyond the rounded rectangular portion in a second direction parallel to the plane of the second semi-rectangular cross section, and the second direction is opposite from the first direction.

In some embodiments, the first semi-rectangular cross section comprises: a first top face and a second top face meeting at a top apex, a first bottom face and a second bottom face meeting at a bottom apex, a first side face joining the first top face to the first bottom face, and a second side face joining the second top face to the second bottom face.

In some embodiments, the top region of the circle portion is defined by at least a first top face and a second top face meeting at a top apex, the bottom region of the circle portion is defined by at least a first bottom face and a second bottom face meeting at a bottom apex, a horizontal region of the rounded rectangular portion is defined by at least a latitudinal width between inner surfaces of a first side face and a second side face, the top apex is disposed above the horizontal region, and the bottom apex is disposed below the horizontal region.

In some embodiments, the first semi-rectangular cross section further comprises a curved segment between each of the first top face and the first side face, the first bottom face and the first side face, the second top face and the second side face, and the second bottom face and the second side face.

In various embodiments, a trocar assembly is provided comprising: an obturator assembly comprising: an obturator housing; an obturator tip; and an obturator body extending from a distal end of the obturator housing to the obturator tip, the obturator body comprising a first semi-rectangular cross section extending from the obturator housing to the obturator tip. The first semi-rectangular cross section comprises: a first top face and a second top face meeting at a top apex, a first bottom face and a second bottom face meeting at a bottom apex, a first side face joining the first top face to the first bottom face, a second side face joining the second top face to the second bottom face, and a tangential angle between tangential segments of each of the first top face, the second top face, the first bottom face, and the second bottom face and a horizontal mid line of the semi-rectangular cross section that is greater than 1.0° (for example from 13.0° to) 19.6°. The trocar assembly further comprises a cannula assembly comprising: a cannula housing; and a cannula sleeve comprising a sleeve body extending from a distal end of the cannula housing, the sleeve body comprising a second semi-rectangular cross section that is offset by at least 0.20 mm from the first semi-rectangular cross section to accommodate insertion of the obturator body within the cannula sleeve.

In some embodiments, the first semi-rectangular cross section further comprises a latitudinal width between outer surfaces of the first side face and the second side face that is from 14.0 mm to 24.0 mm, and a longitudinal height between outer surfaces of the top apex and the bottom apex that is from 9.0 mm to 15.0 mm. Optionally, the first semi-rectangular cross section further comprises a radius of curvature for the top apex and the bottom apex that is from 5.1 R to 7.7 R. Optionally, the first semi-rectangular cross section further comprises a radius of curvature for turns between the first top face and the first side face, the first bottom face and the first side face, the second top face and the second side face, and the second bottom face and the second side face that is from 2.2 R to 3.4 R.

In some embodiments, the sleeve body comprises a distal end having a first opening, a proximal end connected to an interior region of the cannula housing, and the first opening has the second semi-rectangular cross section. In some embodiments, the cannula housing comprises: a distal end having a second opening, a proximal end having a third opening, and a seal located in the interior region between the second opening and the third opening. Optionally, the second opening and the third opening have a third semi-rectangular cross section.

In some embodiments, the semi-rectangular cross section of the second opening and the third opening comprises: a top arced face having a top apex, a bottom arced face having a bottom apex, a first side face joining the top arced face to the bottom arced face, a second side face joining the top arced face to the bottom arced face, a latitudinal width between inner surfaces of the first side face and the second side face that is from 16.0 mm to 26.0 mm, a longitudinal height between inner surfaces of the top apex and the bottom apex that is from 9.0 mm to 15.0 mm, and a radius of curvature for turns between the top arced face and the first side face, the top bottom face and the first side face, the top arced face and the second side face, and the bottom arced face and the second side face that is from 2.2 R to 3.4 R.

In various embodiments, a neuromodulation delivery system is provided comprising: a neuromodulation system comprising an implantable neurostimulator and a lead assembly. The implantable neurostimulator includes a housing having a width of less than 24.0 mm and a height of less than 15.0 mm. The neuromodulation delivery system further comprises a cannula assembly comprising: a cannula housing; and a cannula sleeve comprising a sleeve body extending from a distal end of the cannula housing, the sleeve body comprising a semi-rectangular cross section that is configured to accommodate insertion of the neuromodulation system within the cannula sleeve.

In some embodiments, the semi-rectangular cross section comprises: a first top face and a second top face meeting at a top apex, a first bottom face and a second bottom face meeting at a bottom apex, a first side face joining the first top face to the first bottom face, a second side face joining the second top face to the second bottom face, and a tangential angle between tangential segments of each of the first top face, the second top face, the first bottom face, and the second bottom face and a horizontal mid line of the semi-rectangular cross section that is from 13.0° to 19.6°.

In some embodiments, the semi-rectangular cross section further comprises a latitudinal width between inner surfaces of the first side face and the second side face that is from 15.0 mm to 25.0 mm. Optionally, the semi-rectangular cross section further comprises a longitudinal height between inner surfaces of the top apex and the bottom apex that is from 9.0 mm to 15.0 mm. Optionally, the semi-rectangular cross section further comprises a radius of curvature for the top apex and the bottom apex that is from 5.1 R to 7.7 R. Optionally, the semi-rectangular cross section further comprises a radius of curvature for turns between the first top face and the first side face, the first bottom face and the first side face, the second top face and the second side face, and the second bottom face and the second side face that is from 2.2 R to 3.4 R.

In some embodiments, the sleeve body comprises a distal end having a first opening, a proximal end connected to an interior region of the cannula housing, and the first opening has the semi-rectangular cross section. In some embodiments, the cannula housing comprises: a distal end having a second opening, a proximal end having a third opening, and a seal located in the interior region between the second opening and the third opening. Optionally, the second opening and the third opening have a semi-rectangular cross section.

In some embodiments, the semi-rectangular cross section of the second opening and the third opening comprises: a top arced face having a top apex, a bottom arced face having a bottom apex, a first side face joining the top arced face to the bottom arced face, a second side face joining the top arced face to the bottom arced face, a latitudinal width between inner surfaces of the first side face and the second side face that is from 16.0 mm to 26.0 mm, a longitudinal height between inner surfaces of the top apex and the bottom apex that is from 9.0 mm to 15.0 mm, and a radius of curvature for turns between the top arced face and the first side face, the top bottom face and the first side face, the top arced face and the second side face, and the bottom arced face and the second side face that is from 2.2 R to 3.4 R.

In various embodiments, a method is provided for delivering a neuromodulation system to a site of a target biological structure, the method comprises: inserting an obturator assembly within a cannula assembly, and advancing the obturator assembly to where an obturator housing of the obturator assembly is approximated with a cannula housing of the cannula assembly such that a obturator tip of the obturator assembly protrudes from a distal end of the cannula assembly; applying the obturator tip against tissue such that an arcuate leading surface of the obturator assembly engages the tissue; advancing the obturator assembly and the cannula assembly through the tissue until a portion of the obturator assembly passes through the tissue into a cavity; removing the obturator assembly from the cannula assembly; feeding the neuromodulation system through the cannula assembly to deliver the neuromodulation system to the cavity; inserting one or more surgical instruments into the cannula assembly; and manipulating the one or more surgical instruments to attach a lead assembly of the neuromodulation system to the target biological structure. The cannula assembly comprises a cannula sleeve comprising a first semi-rectangular cross section having: (i) a rounded rectangular portion configured to accommodate feeding the neuromodulation system through the cannula assembly, and (ii) a circular portion configured to accommodate insertion of the one or more surgical instruments through the cannula assembly.

In some embodiments, the obturator assembly comprises an obturator body comprising a second semi-rectangular cross section, wherein the first semi-rectangular cross section has dimensions offset from dimensions of the second semi-rectangular cross section to accommodate insertion of the obturator assembly within the cannula assembly.

In some embodiments, a top region of the circular portion extends above the rounded rectangular portion and a bottom region of the circular portion extends below the rounded rectangular portion.

In some embodiments, a top region of the circular portion extends beyond the rounded rectangular portion in a first direction parallel to a plane of the first semi-rectangular cross section, a bottom region of the circular portion extends beyond the rounded rectangular portion in a second direction parallel to the plane of the first semi-rectangular cross section, and the second direction is opposite from the first direction.

In some embodiments, the first semi-rectangular cross section comprises a first top face and a second top face meeting at a top apex, which define a top region of the circle portion, a first bottom face and a second bottom face meeting at a bottom apex, which define a bottom region of the circle portion, a first side face joining the first top face to the first bottom face, a second side face joining the second top face to the second bottom face, and a latitudinal width between inner surfaces of the first side face and the second side face that is from 15.0 mm to 25.0 mm, which defines a horizontal region of the rectangular portion.

In some embodiments, the first semi-rectangular cross section further comprises a tangential angle between tangential segments of each of the first top face, the second top face, the first bottom face, and the second bottom face and a horizontal mid line of the semi-rectangular cross section that is from 13.0° to 19.6°, and wherein the angle maintains the neuromodulation system in a horizontal position within the rectangular portion and maintains the one or more surgical instruments centered along a longitudinal axis of the circular portion.

BRIEF DESCRIPTION OF THE DRAWINGS

The present invention will be better understood in view of the following non-limiting figures, in which:

FIGS. 1D-1H show an obturator assembly in accordance with various embodiments;

DETAILED DESCRIPTION

I. Introduction

Figure 1A:
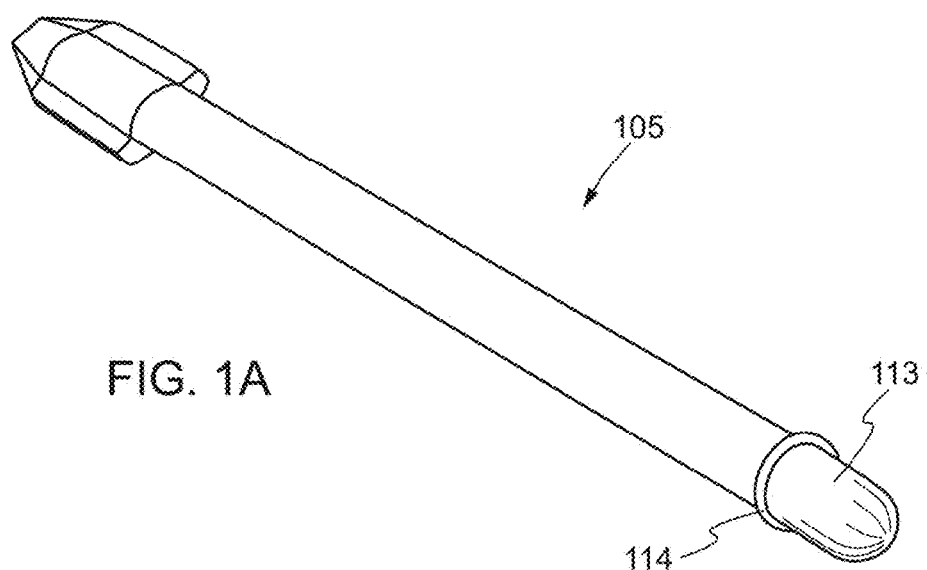
FIGS. 1A-1C show a trocar or laparoscopic port assembly in accordance with various embodiments.

The following disclosure describes systems and methods that allow a user to access a site of a target biological structure in a patient and deliver a medical device or system for neuromodulation to the site of the target biological structure. As used herein, the phrase "target biological structure" refers to any type of vasculature, artery, tissue, or organ. In some embodiments, the target biological structure is a specific neurological site (e.g., a nerve or artery/nerve plexus) targeted for the delivery of a stimulus. As used herein, the term "patient" refers to any multicellular organism, (e.g., an animal ((e.g., a human). As used herein, the term "neuromodulation" means the alteration of nerve activity through targeted delivery of a stimulus, such as electrical stimulation or chemical agents, to specific neurological sites in the patient. A medical device or system for neuromodulation such as a neurostimulator is a device or system having electronic circuit components and/or software configured to deliver the stimulus to the specific neurological site (e.g., a nerve or artery/nerve plexus) via an electrode assembly. One or more portions of the neurostimulator may be implanted in the patient's body. For example, an implanted pulse generator may be encased in a hermetically sealed housing and surgically implanted in the abdominal cavity of the patient. The electrode assembly may be included as a portion of the housing or provided in a separate location and attached to the pulse generator via one or more leads. A neural interface of the electrode assembly may be attached to the target biological structure for delivery of the stimulus from the pulse generator to the target biological structure.

In various embodiments, the systems and methods may be discussed herein in the context of using a laparoscopic procedure to access the abdomen of a patient for implanting and attaching a neurostimulator to the splenic plexus. However, it should be understood that the systems and methods discussed herein may be used in any laparoscopic procedure for any target biological structure. For example, laparoscopic procedures may be performed through very small incisions (usually 0.5-1.5 cm) in the body of the patient to provide access for a trocar or a cannula device. After incision, a cavity (e.g., the abdomen) of the body of a patient may be insufflated with gas in order to expand the cavity to provide a space to perform laparoscopy. In this example, devices may be inserted through the small incision to enable a user, (e.g., a surgeon), to access a site of a target biological structure in a patient for diagnostic or therapeutic purposes (e.g., deliver a medical device or system for neuromodulation to the site of the target biological structure). While the target biological structure is accessed, the user can manipulate, (e.g., visualize, move, modify, ligate, incise, or attach tools to), the target biological structure. In accordance with various aspects discussed herein, the user can deliver a neuromodulation system into the cavity and manipulate, (e.g., visualize, move, modify, or attach tools to), the neuromodulation system in order to implant the pulse generator in the cavity, position the leads, and attach a neural interface to the target biological structure, without causing trauma to the surrounding structures or the target biological structure. In some embodiments, the systems and methods also support the laparoscopic procedure in a manner that provides multidirectional access to various areas of the target biological structure.

In various embodiments, a trocar or a cannula device is provided comprising a cannula housing with an opening at a proximal end, and a cannula sleeve with a sleeve body extending from a distal end of the cannula housing. The sleeve body is essentially a hollow tube with an opening at the distal end and an opening at the proximal end. The interior of the sleeve body is in communication with the cannula housing and is capable of receiving one or more surgical instruments inserted into the opening at the proximal end of the cannula housing through a series of seals. A problem associated with conventional trocars or cannula devices is that the cross section of the cannula sleeve, openings of the cannula sleeve, and seals and opening(s) of the cannula housing are designed to fit one or more conventional surgical instruments. For example, conventional trocars or cannula devices typically have a circular cross section with a given diameter and the valves are configured to create a seal around surgical instruments from that diameter to a minimum diameter. These systems and approaches are thus limited in the shape or cross section of objects (e.g., a neuromodulation system) that can be inserted into the cannula housing and fed through the cannula sleeve.

To address these problems, a trocar or a cannula device is provided comprising a cannula housing with an opening at a proximal end, and a cannula sleeve with a sleeve body extending from a distal end of the cannula housing. The cross section of the cannula sleeve, openings of the cannula sleeve and opening(s) of the cannula housing are designed having a semi-rectangular cross section comprising: (i) a rounded rectangular portion, and (ii) a circular portion. Alternatively, the cross section of the cannula sleeve, openings of the cannula sleeve and opening(s) of the cannula housing are designed having a semi-obround cross section comprising: (i) an obround portion, and (ii) a circular portion. The rounded rectangular portion or the obround portion is configured to accommodate feeding the neuromodulation system through the trocar or cannula device, and the circular portion is configured to accommodate insertion of the one or more surgical instruments through the trocar or cannula device. In some embodiments, the semi-rectangular cross section or the semi-obround cross section further comprises a tangential angle between a horizontal mid line of the semi-rectangular cross section or the semi-obround cross section and each of the top faces and the bottom faces that is from 13.0° to 19.6°. The tangential angle is thus configured to maintain the neuromodulation system in a horizontal position within the rounded rectangular portion or the obround portion during delivery and maintain the one or more surgical instruments centered along a longitudinal axis of the circular portion during manipulation.

One illustrative embodiment of the present disclosure comprises: a cannula housing comprising a first opening at a proximal end, and a cannula sleeve comprising a sleeve body extending from a distal end of the cannula housing, the sleeve body comprising a distal end having a second opening, a proximal end connected to the cannula housing, and a semi-rectangular cross section extending from the proximal end of the sleeve body to the distal end of the sleeve body. The semi-rectangular cross section comprises: (i) a rounded rectangular portion, and (ii) a circular portion. The circular portion extends beyond the rounded rectangular portion in a direction parallel to a plane of the semi-rectangular cross section. In some embodiments, a top region of the circular portion extends beyond the rounded rectangular portion in a first direction parallel to the plane of the semi-rectangular cross section and a bottom region of the circular portion extends beyond the rounded rectangular portion in a second direction parallel to the plane of the semi-rectangular cross section, and the second direction is opposite from the first direction.

Another illustrative embodiment of the present disclosure comprises: a cannula housing comprising a distal end, a proximal end having a first opening, and an interior region between the distal end and the proximal end, and a cannula sleeve comprising a sleeve body extending from the distal end of the cannula housing, the sleeve body comprising a distal end having a second opening, a proximal end connected to the interior region of the cannula housing, and a semi-rectangular cross section extending from the proximal end of the sleeve body to the distal end of the sleeve body. The semi-rectangular cross section comprises: a first top face and a second top face meeting at a top apex, a first bottom face and a second bottom face meeting at a bottom apex, a first side face joining the first top face to the first bottom face, a second side face joining the second top face to the second bottom face, and a tangential angle between a horizontal mid line of the semi-rectangular cross section and each of the first top face, the second top face, the first bottom face, and the second bottom face is an acute angle.

Another illustrative embodiment of the present disclosure comprises: a cannula housing comprising a first opening at a proximal end, and a cannula sleeve comprising a sleeve body extending from a distal end of the cannula housing, the sleeve body comprising a distal end having a second opening, a proximal end connected to the cannula housing, and a semi-obround cross section extending from the proximal end of the sleeve body to the distal end of the sleeve body. The semi-obround cross section comprises: (i) an obround portion, and (ii) a circular portion. A top region of the circle portion is defined by a first top face and a second top face meeting at a top apex, a bottom region of the circle portion is defined by a first bottom face and a second bottom face meeting at a bottom apex, a horizontal region of the obround portion is defined by a latitudinal width between inner surfaces of a first side face and a second side face, and a tangential angle between a horizontal mid line of the semi-obround cross section and each of the first top face, the second top face, the first bottom face, and the second bottom face is an acute angle.

Advantageously, these approaches provide trocar or cannula devices and systems that are capable of receiving and delivering a neuromodulation system to a cavity of a patient, and also receiving one or more surgical instruments for carrying out one or more laparoscopic procedures (e.g., tissue dissection, neurostimulator implant, attachment of electrodes, etc.). Moreover, these approaches allow the neuromodulation system to be maintained in a substantially horizontal position within the rounded rectangular portion or the obround portion of cross section during delivery. Also advantageously, these approaches allow for the one or more surgical instruments to be maintained substantially centered along a longitudinal axis of the circular portion cross section during manipulation.

II. Laparoscopic Port Systems and Devices

Figure 1B:
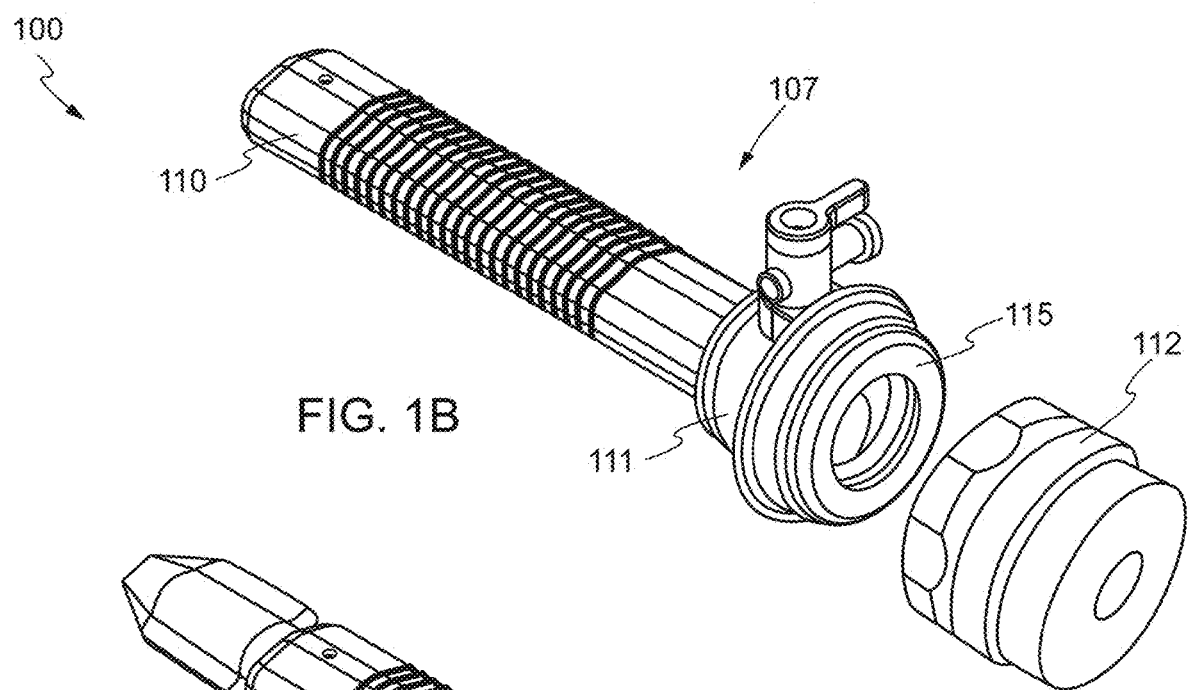
Figure 1C:
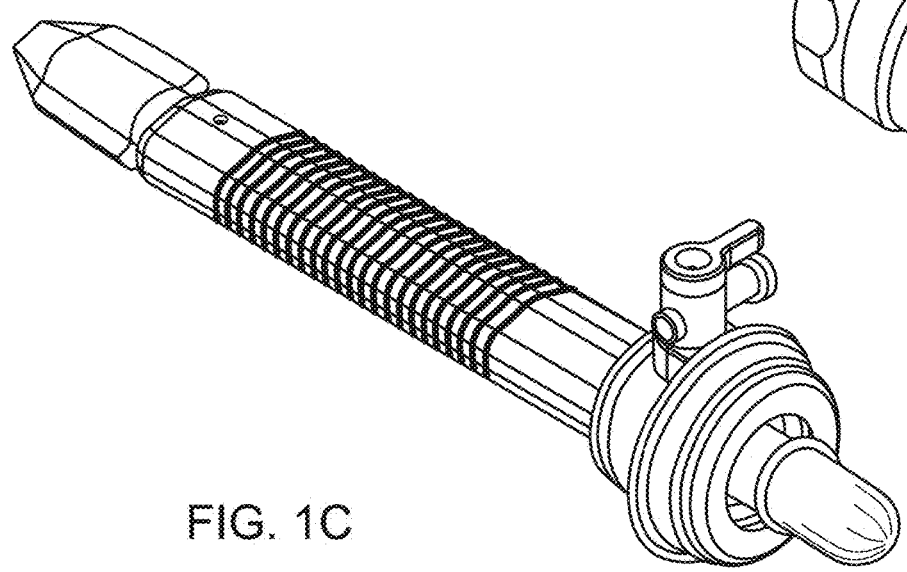

FIGS. 1A-1C show a trocar or laparoscopic port assembly 100 for accessing a site of a target biological structure in accordance with various aspects. Trocar assembly 100 is particularly adapted for use in minimally invasive surgical procedures such as endoscopic or laparoscopic procedures for the implantation of a neuromodulation system in a cavity of a body. In various embodiments, the trocar assembly 100 includes two principal subassemblies, namely, an obturator assembly 105 and a cannula assembly 107. As shown in FIG. 1B, cannula assembly 107 includes a sleeve 110, a first portion of a cannula housing 111, and a second portion of the cannula housing 112. The second portion of the cannula housing 112 is removable from the first portion of the cannula housing 111 such that the obturator assembly 105 can be engaged with the cannula assembly 107. As shown in FIG. 1C, the obturator assembly 105 is arranged to be inserted within the cannula assembly 107 and advanced to where an obturator handle 113 is approximated with the first portion of a cannula housing 111 such that a tip of the obturator assembly 105 protrudes from the distal end of the cannula assembly 107. A shoulder 114 of the obturator handle 113 may be appropriately dimensioned to form a friction fit with annular element 115 of the first portion of the cannula housing 111 or may be coupled to each other by conventional means including bayonet coupling, tongue-groove, etc. The obturator assembly 105 is used to create an opening in the abdominal wall through which a portion of the cannula assembly 107 is inserted and fixed into place. The obturator assembly 105 may then be removed from the sleeve 110 and the first portion of the cannula housing 111 to allow insertion of a neuromodulation system and laparoscope or other surgical instruments through the sleeve 110 and the first portion of the cannula housing 111.

With reference now to FIGS. 1D-1H, the obturator assembly 105 includes an obturator handle 113, an obturator body 120 having a proximal end 125 attached to the obturator handle 113 and extending distally from the obturator handle 113, and an obturator tip 130 disposed at a distal end 135 of the obturator body 120. As used herein, the term "proximal end" refers to a first end of the main body, while the term "distal end" refers to a second end opposing the first end. For example, the proximal end may be an end of the main body, which is closest to the user, and the distal end may be an end of the main body, which is furthest from the user. The obturator assembly 105 from the obturator handle 113 to the obturator tip 130 has a length (L1) of at least 105 mm, for example from 105 mm to 165 mm or from 130 mm to 180 mm (see, e.g., FIG. 1B). Each of the obturator handle 113, the obturator body 120, and the obturator tip 130 may be opaque in part or in whole and/or transparent in part or in whole, and may be fabricated from biocompatible metal and/or polymeric material.

In various embodiments, the obturator handle 113 includes a shoulder 114 at a distal end 145 and a base 150 at a proximal end 155. As shown in FIG. 1E, the shoulder 114 may be annular in shape having a diameter (D1) of at least 28 mm, for example from 28 mm to 55 mm, 30 mm to 45 mm, or from 35 mm to 40 mm. The base 150 may also be annular in shape having a diameter (D2) of at least 24 mm, for example from 24 mm to 45 mm, 28 mm to 35 mm, or from 30 mm to 40 mm. The obturator handle 113 may be grasped by a user to advance and drive the obturator tip 130 and the obturator body 120 through the tissue of a patient.

In various embodiments, the obturator body 120 from the proximal end 125 to the distal end 135 has a length (L2) of at least 100 mm, for example from 100 mm to 150 mm or from 120 mm to 170 mm. In some embodiments, at least a portion of the obturator body 120 (e.g., a portion towards the distal end 135) has a height (H1) from 9.6 mm to 14.4 mm, for example 11.5 mm, 12 mm, or 12.1 mm, and a semi-rectangular cross section B-B (see, e.g., FIGS. 1D, 1E, and 1H). As used herein, the term "semi-rectangular" or "semi-rectangular cross section" means a rounded rectangular portion overlaid onto a larger central circular portion, as shown in FIG. 1I. As used herein, the term "rounded rectangle" or "rounded rectangular portion" means a shape obtained by taking the convex surface of four equal circles of radius r and placing their centers at the four corners of a rectangle with side lengths a and b and creating a perimeter p around the surface of the four equal circles and the rectangle, where the perimeter p of the shape is equal to $2(a+b+\pi r)$, as shown in FIG. 1J. While the semi-rectangular cross section of various structures is described herein in particular detail with respect to several described embodiments, it should be understood that other shapes or cross sections of the various structures (e.g., the portion of the obturator body 120) have been contemplated without departing from the spirit and scope of the present invention. For example, a semi-obround cross section may be used alone or in combination with the semi-rectangular cross section for at least some of the structures of the trocar or laparoscopic port assembly 100. As used herein, the term "semi-obround" or "semi-obround cross section" means an obround portion overlaid onto a larger central circular portion, as shown in FIG. 1K.

The dimensions of the semi-rectangular cross section (or semi-obround cross section) are configured to allow the obturator body 120 to slide through the sleeve 110 and the first portion of the cannula housing 111 in an unobstructed manner, as discussed in detail herein. As shown in FIG. 1H, the semi-rectangular cross section comprises top faces 160, 162, bottom faces 165, 167, side faces 170, 172, and apexes 175, 177 between the top faces 160, 162 and the bottom faces 165, 167, respectively. In various embodiments, the rounded rectangular portion has a horizontal region that is defined by at least a latitudinal (horizontal) width (W1) between inner surfaces of side faces 170, 172. The width (W1) may be from 14 mm to 24 mm, for example, 16.8 mm, 20 mm, or 20.5 mm. In some embodiments, the horizontal region of the rounded rectangular portion is further defined by a longitudinal (vertical) height (H1) between inner surfaces of the top and bottom surface of the rounded rectangular portion, as illustrated in FIG. 1I.

In various embodiments, the circular portion has a diameter defined between the apexes 175, 177. The diameter may be from 9.0 mm to 14.0 mm, for example, 11.5 mm, 12 mm, or 12.1 mm. The longitudinal height (H1) of the rounded rectangular portion is less than the diameter of the circular portion. More specifically, the top apex 175 is disposed above the horizontal region of the rounded rectangular portion, and the bottom apex 177 is disposed below the horizontal region of the rounded rectangular portion. Consequently, the circular portion of the semi-rectangular cross section extends beyond the rounded rectangular portion in a direction parallel to a plane of the semi-rectangular cross section. In some instances, a top region of the circular portion extends beyond the rounded rectangular portion in a first direction parallel to the plane of the semi-rectangular cross section and a bottom region of the circular portion extends beyond the rounded rectangular portion in a second direction parallel to the plane of the semi-rectangular cross section. The second direction may be opposite from the first direction. For e example, a top region of the circular portion may extend above the rounded rectangular portion and a bottom region of the circular portion may extend below the rounded rectangular portion (as shown in FIG. 1I).

In various embodiments, the apexes 175, 177 are part of a first set of curved segments of the semi-rectangular cross section. The first set of curved segments comprising the apexes 175, 177 may have a radius of curvature (R1) that is from 5.1 R to 7.7 R, for example 6.0 R, 6.4 R, or 6.6 R. In various embodiments, the semi-rectangular cross section further comprises a second set of curved segments defined by the convex surface of the four equal circles of radius r (i.e., the turns from the side faces 170, 172 to the top faces 160, 162 and bottom faces 165, 167). The curved segments of the second set of curved segments are located between each of the first top face and the first side face, the first bottom face and the first side face, the second top face and the second side face, and the second bottom face and the second side face. The second set of curved segments may have a radius of curvature (R2) from 2.2 R to 3.4 R, for example, 2.4 R, 2.8 R, or 3.0 R.

In some embodiments, the top faces 160, 162 and the bottom faces 165, 167 are segments formed tangentially to the convex surface of the four equal circles of radius r at a given point. In certain embodiments, the tangential angle (A1) between the tangential segments of each of the top faces 160, 162 and the bottom faces 165, 167 and a horizontal mid line 180 of the semi-rectangular cross section is an acute angle (i.e., less than 90.0° but greater than 0.0°). In some embodiments, the acute angle is greater than 1.0°. In some embodiments, the acute angle is from 13.0° to 19.6°, for example 16.0°, 16.3°, or 16.6°. The top faces 160, 162 and the top apex 175 define a top region of the circle portion of the semi-rectangular cross section. The bottom faces, 165, 167 and the bottom apex 177 define a bottom region of the circle portion of the semi-rectangular cross section. The radius of curvature (R1) for the apexes 175, 177 defines a radius of curvature for a top portion and a bottom portion of the circle portion of the semi-rectangular cross section. The radius of curvature (R2) for the convex surface of the four equal circles of radius r defines a radius of curvature for the corners of the rounded rectangular portion. The tangential segments of each of the top faces 160, 162 and the bottom faces 165, 167 are configured to join the circular portion with the rounded rectangular portion while maintaining a smooth outer surface for sealing. The tangential angle (A1) maintains the neuromodulation system in a horizontal position within the rounded rectangular portion and maintains the one or more surgical instruments centered along a longitudinal axis of the circular portion.

Figure 1F:
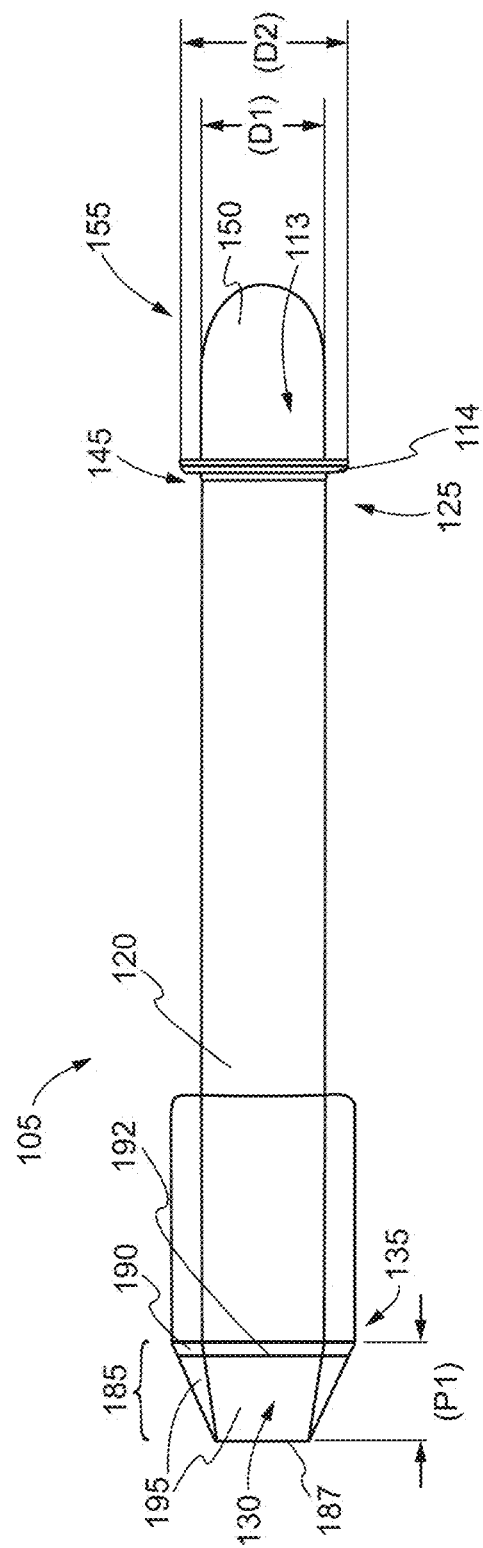
Figure 1G:
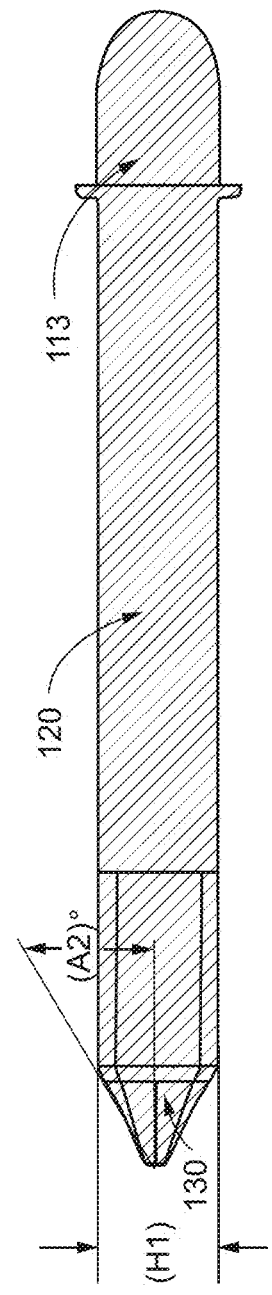
Figure 1H:
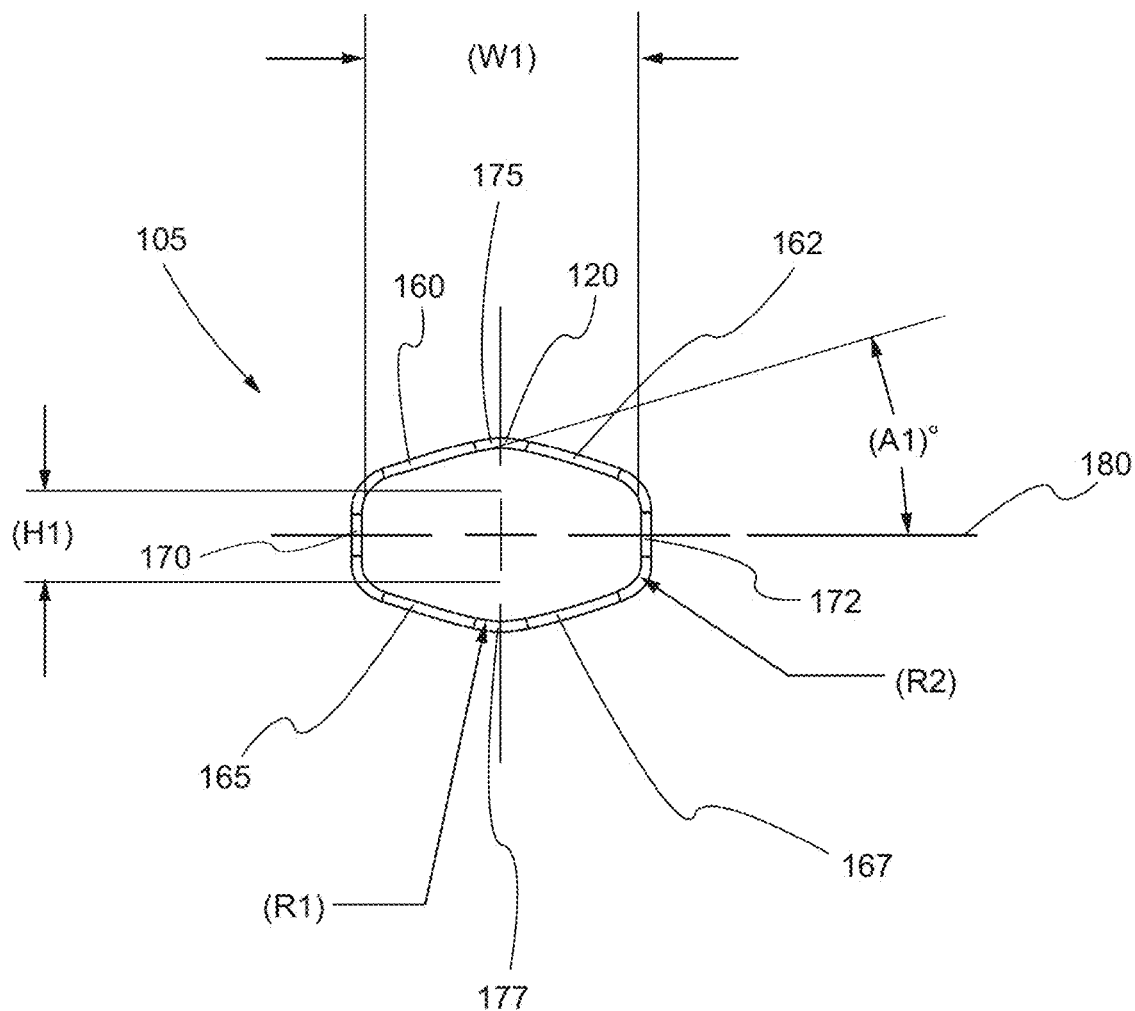
Figure 1I:
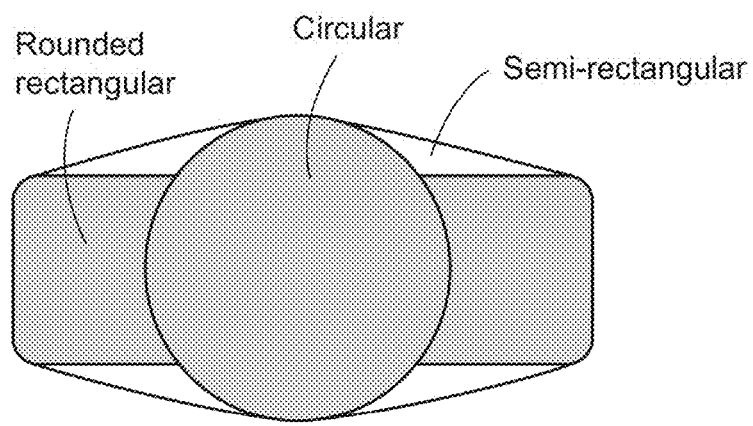
FIG. 1I shows a semi-rectangular cross section in accordance with various embodiments.
Figure 1J:
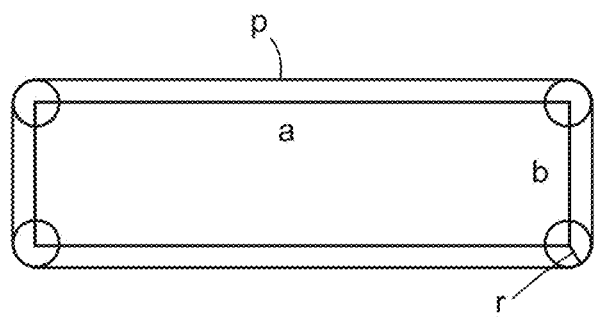
FIG. 1J shows a rounded rectangle in accordance with various embodiments.
Figure 1K:
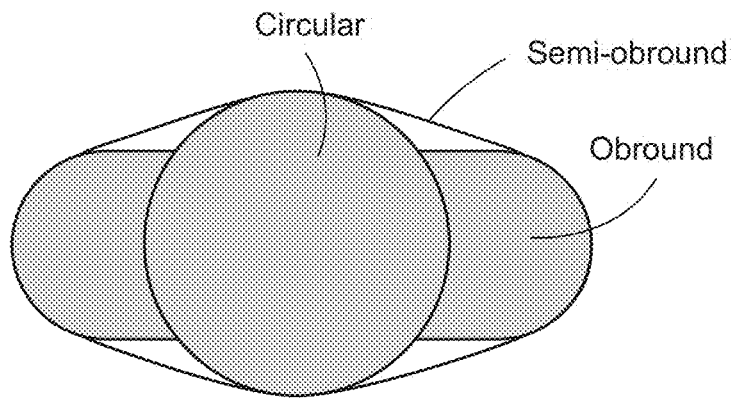
FIG. 1K shows a semi-obround cross section in accordance with various embodiments.

In various embodiments, the obturator tip 130 includes dissecting segment 185 extending to arcuate leading surface 187 (see, e.g., FIGS. 1E and 1F). The arcuate leading surface 187 is atraumatic to tissue and is spaced from the obturator body 120 a predetermined distance (P1) of 0.5 mm to 2.5 mm, for example 1.0 mm, 1.5 mm, or 2.0 mm. This consequent narrow profile provided by obturator tip 130 permits initial insertion of a portion of the obturator assembly 105 within the tissue and facilitates, e.g., dissection or advancement within the tissue without an incising action. Planar dissecting segment 185 includes opposed outer surfaces 190 having a planar cross section, which extend from the obturator body 120 to a taper boundary 192 of the dissecting segment 185. Outer surfaces 190 define a substantially symmetrical or linear arrangement, e.g., the contour of the opposed outer surface may define a linear rectangular shape. Planar dissecting segment 185 further includes opposed tapered surfaces 195 having a planar cross section, which extend from the taper boundary 192 to the arcuate leading surface 187. Opposed tapered surfaces 195 may have an angle (A2) (see, e.g., FIG. 1G) from the arcuate leading surface 187 from 20.0° to 65.0°, for example 45.0°, 40.0°, or 35.0° and function as a dissecting element to dissect tissue as arcuate leading surface 187 is advanced into tissue.

Figure 2A:
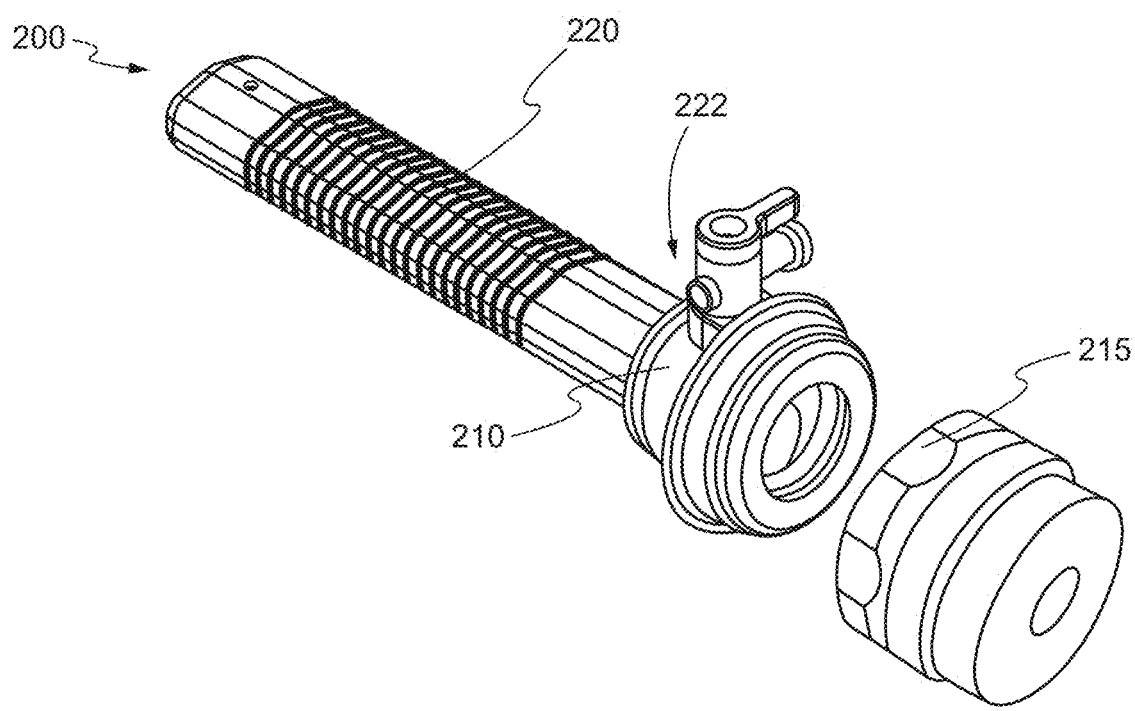
FIGS. 2A-2L show a cannula assembly in accordance with various embodiments.
Figure 2B:
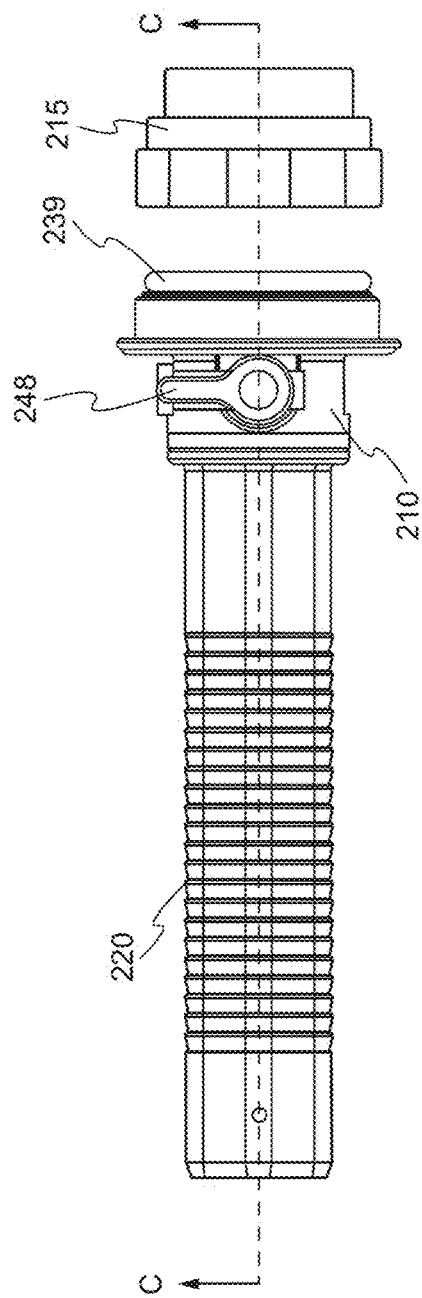
Figure 2C:
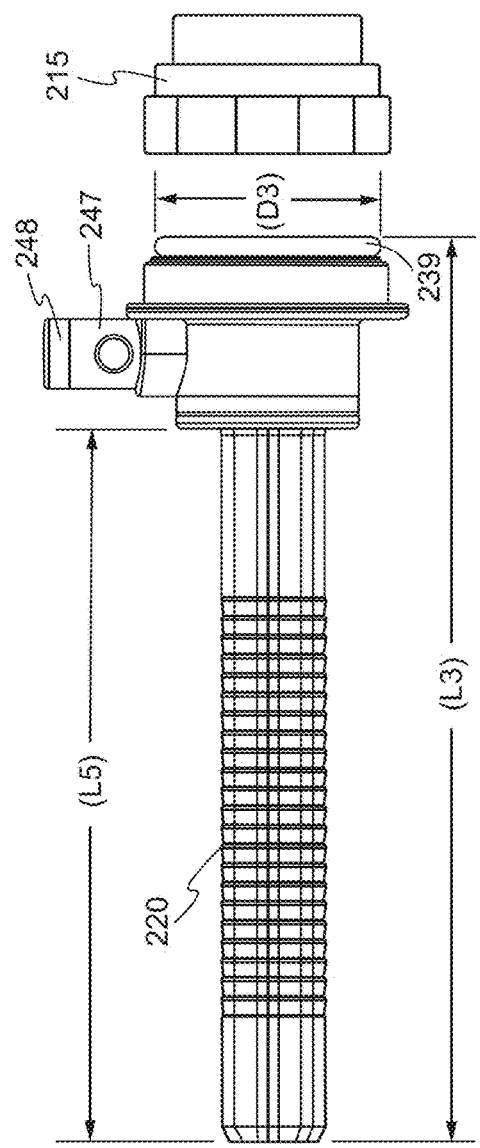
Figure 2D:
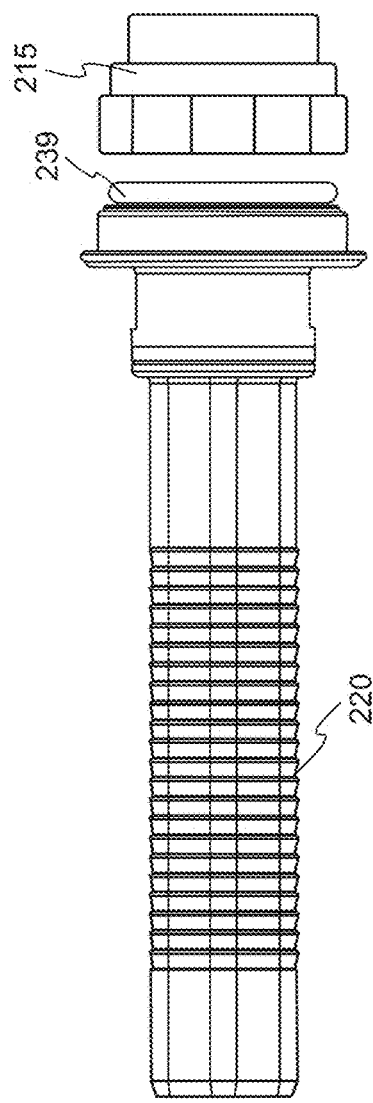
Figure 2E:
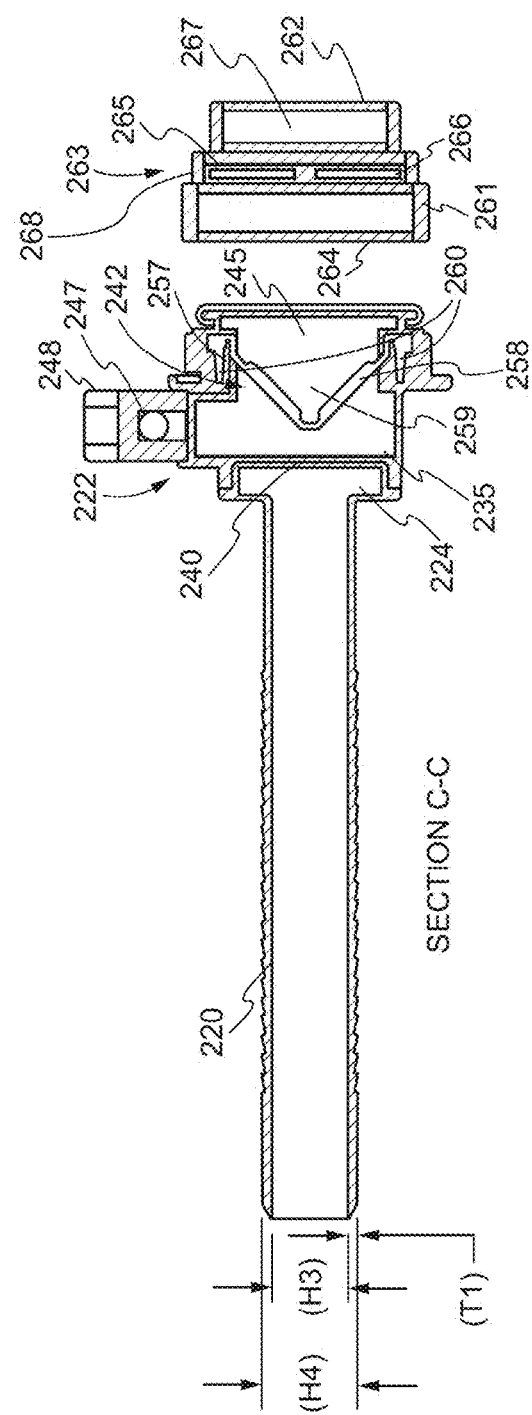
Figure 2F:
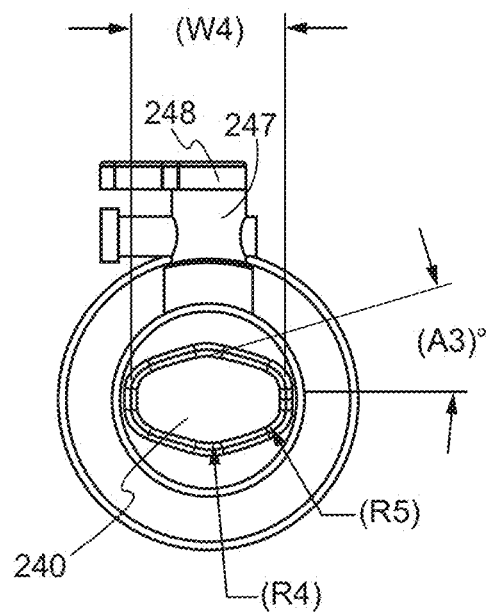

With reference now to FIGS. 2A-2L, the cannula assembly 200 (e.g., the cannula assembly 107 described with respect to FIG. 1B) includes a first portion of the cannula housing 210, a second portion of the cannula housing 215, and cannula sleeve 220 extending from the distal end 222 of the first portion of the cannula housing 210. One or more of the first portion of the cannula housing 210, the second portion of the cannula housing 215, and the cannula sleeve 220 may be opaque in part or in whole and/or transparent in part or in whole, and may be fabricated from biocompatible metal and/or polymeric material. In various embodiments, the cannula sleeve 220 includes a hub 224, sleeve body 225 having a proximal end 226 attached to the hub 224 and extending distally from the hub 224, an opening 227 disposed at a distal end 228 of the sleeve body 225, and an opening 229 disposed at the proximal end 226 of the sleeve body 225 (see, e.g., FIGS. 2E and 2H-2L). In some embodiments, the sleeve body 225 may include non-patterned portions 230 and an anti-slip pattern or locking ribs 232 on external surface 234 (see, e.g., FIGS. 2I and 2J). The anti-slip pattern or locking ribs 232 may be adapted to facilitate retention of the cannula sleeve 220 within the tissue. The first portion of the cannula housing 210 and the cannula sleeve 220 may be mechanically interfitted to form a portion of the cannula assembly 200. For example, as shown in FIG. 2E, the first portion of the cannula housing 210 may include a slot 235 at the distal end 222 that matches the size and shape of the hub 224 such that the hub 224 sits within the slot 235 for securing the cannula sleeve 220 to the cannula housing 210. The cannula assembly 200 from the first portion of the cannula housing 210 to the opening 227 may have a length (L3) of at least 105 mm, for example 125 mm, 143.3 mm, or 180 mm (see, e.g., FIG. 2C).

As shown in FIGS. 2B-2G, the first portion of the cannula housing 210 may further include an annular element 239 (e.g., the annular element 115 discussed with respect to FIG. 1B)), a distal opening 240, a seal assembly 242, a proximal opening 245, a stop-cock valve 247, and a stop-cock switch 248. The annular element 239 may have a diameter (D3) of at least 20 mm, for example from 20 mm to 45 mm, 25 mm to 40 mm, or from 30 mm to 45 mm such that the first portion of the cannula housing 210 may be coupled to the obturator handle. In various embodiments, the distal opening 240 and the proximal opening 245 have a semi-rectangular cross section to substantially match the cross section of a portion of the obturator body 120 and allow for the obturator body 120 to pass through the cannula housing 210 without obstruction (see, e.g., FIGS. 2F and 2G). In some embodiments, at least some of the dimensions of the distal opening 240 and the proximal opening 245 are slightly larger than the dimensions of the portion of the obturator body 120 to provide a semi-rectangular gap between the distal opening 240 and the portion of the obturator body 120 and between the proximal opening 245 and the obturator body 120. Slightly larger is defined as an offset of at least 0.01 mm but no more than 1.0 mm. The offset may be between 0.05 mm and 0.90 mm, for example about 0.15 mm, about 0.30 mm, about 0.55 mm, or about 0.70 mm. As used herein, the terms "substantially," "approximately" and "about" are defined as being largely but not necessarily wholly what is specified (and include wholly what is specified) as understood by one of ordinary skill in the art. In any disclosed embodiment, the term "substantially," "approximately," or "about" may be substituted with "within [a percentage] of" what is specified, where the percentage includes 0.1, 1, 5, and 10 percent.

Figure 2G:
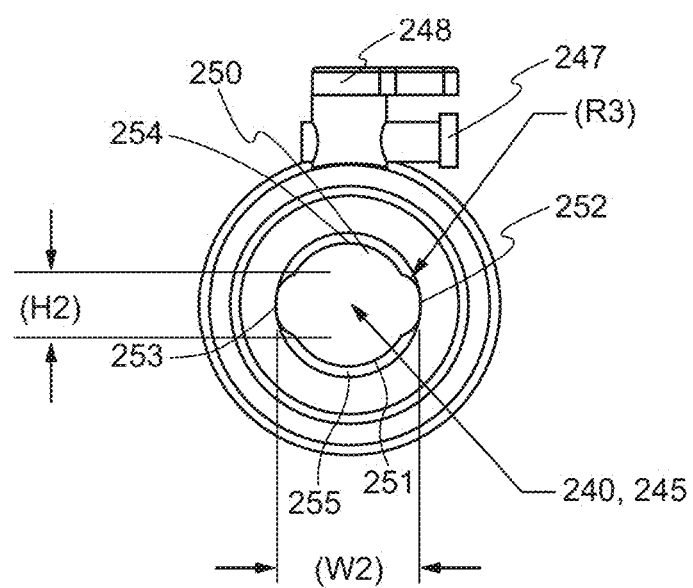
Figure 2H:
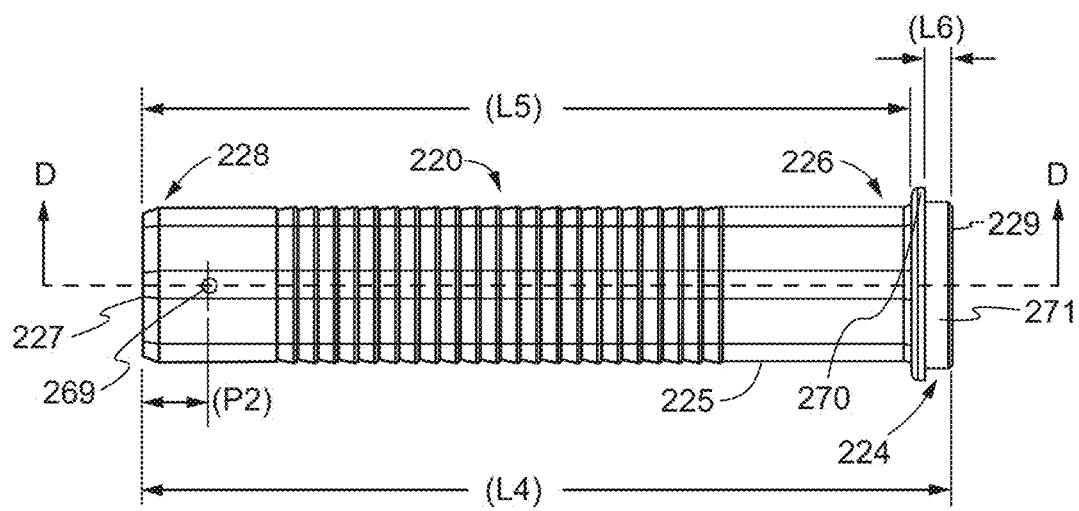
Figure 2I:
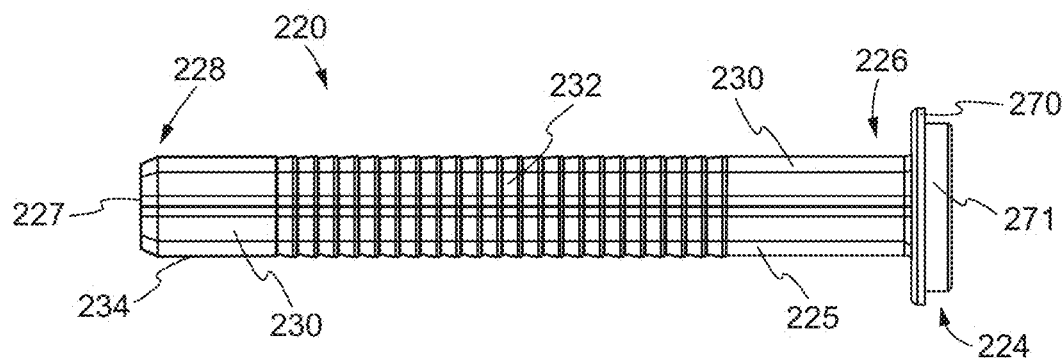
Figure 2J:
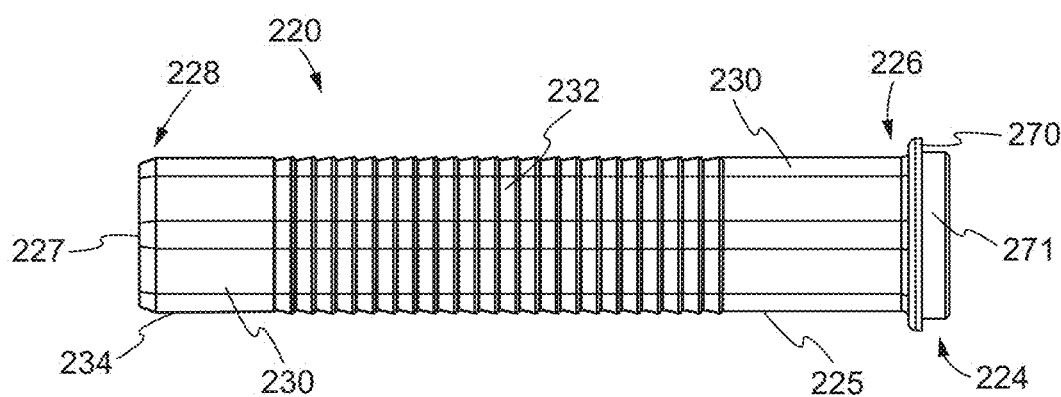
Figure 2K:
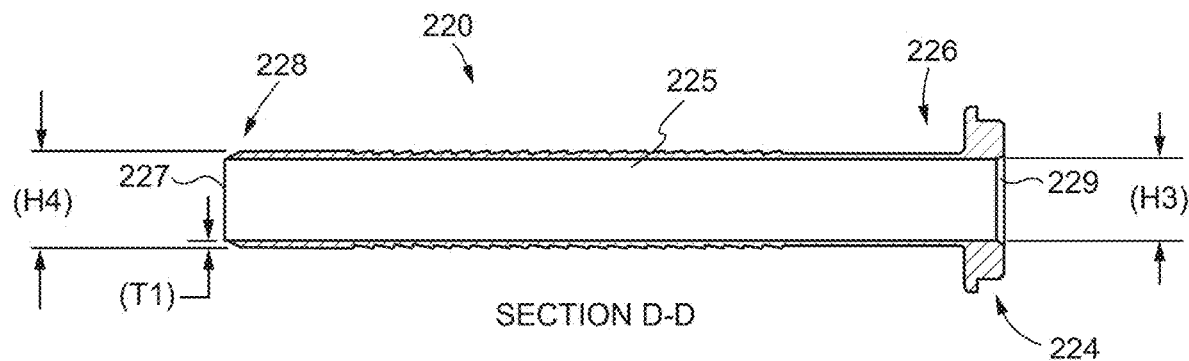

FIG. 2G shows the distal opening 240 and/or the proximal opening 245 may comprise top arced face 250, bottom arced face 251, side faces 252, 253, and apexes 254, 255. Side faces 252, 253 join the top arced face 250 to the bottom arced face 251. In various embodiments, the rounded rectangular portion of the distal opening 240 and/or the proximal opening 245 has a horizontal region that is defined by at least a latitudinal (horizontal) width (W2) between inner surfaces of the side faces 252, 253. The width (W2) may be from 16.0 mm to 26.0 mm, for example 18.0 mm, 21.0 mm, or 23.5 mm. In some embodiments, the horizontal region of the rounded rectangular portion is further defined by a longitudinal (vertical) height (H2) of the top and bottom surface of the rounded rectangular portion, as illustrated in FIG. 1I.

In various embodiments, the circular portion has a diameter defined between the apexes 254, 255. The diameter may be from 9.0 mm to 15.0 mm, for example 11.0 mm, 12.3 mm, or 13.5 mm. The longitudinal height (H2) of the rounded rectangular portion is less than the diameter of the circular portion. More specifically, the top apex 254 is disposed above the horizontal region of the rounded rectangular portion, and the bottom apex 255 is disposed below the horizontal region of the rounded rectangular portion. Consequently, the circular portion of the semi-rectangular cross section extends beyond the rounded rectangular portion in a direction parallel to a plane of the semi-rectangular cross section. In some instances, a top region of the circular portion extends beyond the rounded rectangular portion in a first direction parallel to the plane of the semi-rectangular cross section and a bottom region of the circular portion extends beyond the rounded rectangular portion in a second direction parallel to the plane of the semi-rectangular cross section. The second direction may be opposite from the first direction. For e example, a top region of the circular portion may extend above the rounded rectangular portion and a bottom region of the circular portion may extend below the rounded rectangular portion (as shown in FIG. 1I).

In various embodiments, the apexes 254, 255 are part of a first set of curved segments of the semi-rectangular cross section (i.e., the top arced face 250 and the bottom arced face 251). The first set of curved segments comprising the apexes 254, 255 may have a radius of curvature (R1) that is greater than 5.0 R, for example 6.0 R, 7.4 R, or 8.6 R. In various embodiments, the semi-rectangular cross section further comprises a second set of curved segments from the side faces 252, 253 to the top arced face 250, and from the side faces 252, 253 to the bottom arced face 251. The second set of curved segments may have a radius of curvature (R3) from 2.2 R to 3.4 R, for example 2.4 R, 2.8 R, or 3.0 R. The radius of curvature (R3) for the curved segments defines a radius of curvature for portions of the turns of the rounded rectangular portion.

In various embodiments, as shown in FIG. 2E, the seal assembly 242 is integrated or releasably mounted within the cannula housing 210. The stop-cock valve 247 and the and stop-cock switch 248 allow and prevent the passage of an insufflation gas, (e.g. carbon dioxide), through tubing into a portion of the first portion of the cannula housing 210 that is distal of the seal assembly 242. The seal assembly 242 may include a seal housing 257 and at least one internal seal 258 such as a duck-bill valve or other zero closure valve adapted to close in the absence of a surgical instrument to prevent passage of insufflation gases through the cannula assembly 200. In some embodiments, the seal housing 257 defines a longitudinal opening 259 between the distal opening 240 and the proximal opening 245 to permit passage of a neuromodulation system and surgical instrumentation through the seal housing 257. The seal housing 257 may include a mount 260 that houses seal 258 and is adapted for angular movement relative to the central longitudinal axis of the seal housing 257 upon angulation of the neuromodulation system and the surgical instrument while seal 258 substantially maintains a sealed reception about the neuromodulation system and the surgical instrument introduced through the proximal opening 245 and into the cannula sleeve 220.

As shown in FIGS. 2B-2E, the second portion of the cannula housing 215 may include an annular element 261, a distal opening 262, a seal assembly 263, and a proximal opening 264. The annular element 261 may be configured such that the second portion of the cannula housing 215 may be coupled to the first portion of the cannula housing 210. In various embodiments when the second portion of the cannula housing 215 is coupled to the first portion of the cannula housing 210, the interior of the second portion of the cannula housing 215 is in communication with the interior of the first portion of the cannula housing 210 and is capable of receiving one or more surgical instruments inserted into the proximal opening 264. The seal assembly 263 may include a seal housing 265 and at least one internal seal 266 such as an O-ring that is open in the absence of a surgical instrument. In some embodiments, the seal housing 265 defines a longitudinal opening 267 between the distal opening 262 and the proximal opening 264 to permit passage of a surgical instrument through the seal housing 265. The seal housing 265 may include a mount 268 that houses seal 266 and is adapted for angular movement relative to the central longitudinal axis of the seal housing 265 upon angulation of the surgical instrument while seal 266 substantially maintains a sealed reception about the surgical instrument introduced through the proximal opening 264 and into the second portion of the cannula housing 215.

As shown in FIGS. 2H-2L, the cannula sleeve 220 may include the hub 224, the sleeve body 225, the distal opening 227, the proximal opening 229, and a vent hole 269. The cannula sleeve 220 may have a length (L4) from 105 mm to 180 mm, for example, 105.0 mm, 118.7 mm, or 127.0 mm (see, e.g., FIG. 2H). The sleeve body 225 may have a length (L5) from 95 mm to 165 mm, for example, 105.0 mm, 112.7 mm, or 125.0 mm, and a wall thickness (Ti) at the non-patterned portions 230 from 0.3 mm to 2.0 mm, for example, 0.5 mm, 0.9 mm, or 1.2 mm (see, e.g., FIGS. 2H and 2K). In various embodiments, the hub 224 includes an annular ring 270 and a base element 271. The annular ring 270 may have a diameter (D4) from 25 mm to 50 mm, for example, 27.0 mm, 28.5 mm, or 32.0 mm such that the hub 224 seals with the first portion of the cannula housing 210 (see, e.g., FIG. 2L). The base element 271 may have a diameter (D5) from 20 mm to 45 mm, for example 23.0 mm, 24.5 mm, or 26.0 mm such that the base element 271 fits into the slot 235 (see, e.g., FIG. 2L). The base element 271 may have a length (L6) from 2 mm to 6 mm, for example, 3.0 mm, 4.0 mm, or 5.0 mm (see, e.g., FIG. 2H). In some embodiments, the vent hole 269 is spaced a predetermined distance (P2) from the distal opening 227. The predetermined distance (P2) may be from 7.0 mm to 13.0 mm, for example 8.0 mm, 9.7 mm, or 11.0 mm.

In various embodiments, the sleeve body 225, the distal opening 227, and the proximal opening 229 have a semi-rectangular cross section that is sized and shaped such that the obturator body 120 can extend completely through the cannula sleeve 220 without obstruction. Additionally, insufflation fluid, which passes through the stop-cock valve 247 and the first portion of the cannula housing 210, can pass through a semi-rectangular gap created between the cannula sleeve 220 and the obturator body 120 by the slightly larger size of the internal diameter of the cannula sleeve 220 in relation to the outer diameter of the obturator body 120. In some embodiments, at least some of the dimensions of the sleeve body 225, the distal opening 227, and the proximal opening 229 are slightly larger than the dimensions of the obturator body 120 to provide the semi-rectangular gap between each of the sleeve body 225, the distal opening 227, and the proximal opening 229 and the obturator body 120. In certain embodiments, slightly larger is defined as an offset of at least 0.05, at least 0.20, or about 0.05 mm to about 0.50 mm, for example about 0.15 mm, about 0.20 mm, about 0.25 mm, or about 0.30 mm.

Figure 2L:
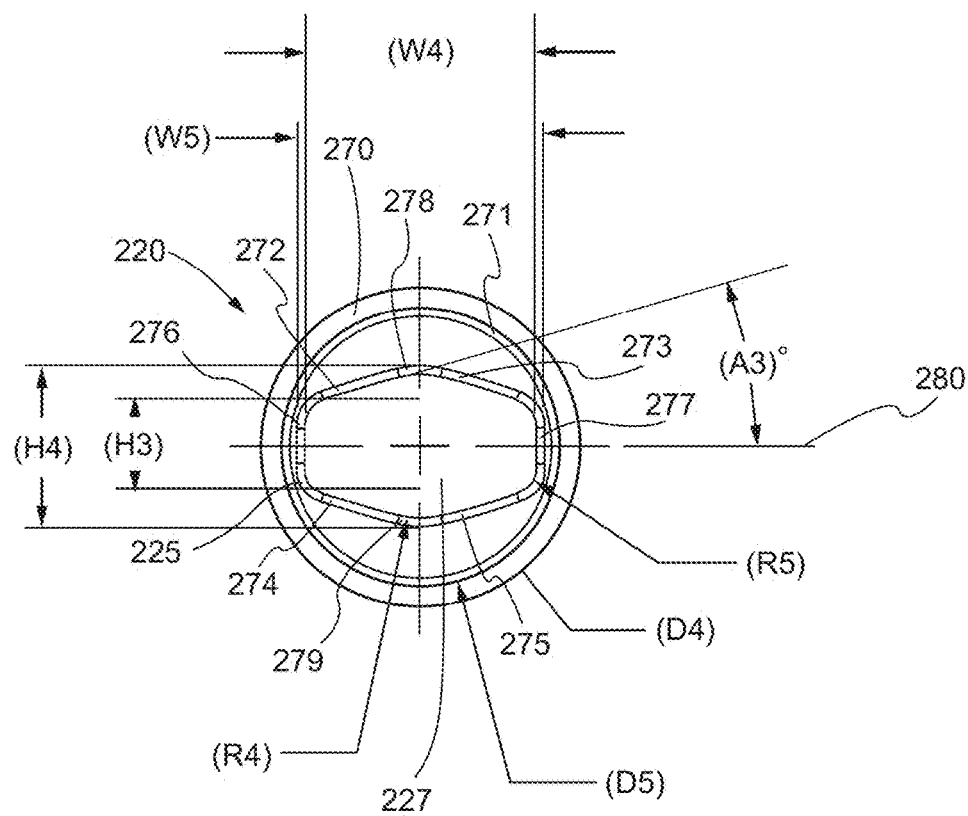

FIG. 2L shows the semi-rectangular cross section of each of the sleeve body 225 and the distal opening 227. The semi-rectangular cross section comprises top faces 272, 273, bottom faces 274, 275, side faces 276, 277, and apexes 278, 279 between the top faces 272, 273 and the bottom faces 274, 275, respectively. In various embodiments, the rounded rectangular portion has a horizontal region that is defined by at least a latitudinal (horizontal) width (W4) between inner surfaces of the side faces 276, 277. The width (W4) may be from 15 mm to 25 mm, for example 18.5 mm, 21 mm, or 22.5 mm. In some embodiments, the horizontal region of the rounded rectangular portion is further defined by a latitudinal (horizontal) width (W5) between outer surfaces of the side faces 276, 277. The width (W5) may be from 13 mm to 27 mm, for example 17.5 mm, 22.8 mm, or 25.0 mm. In some embodiments, the horizontal region of the rounded rectangular portion is further defined by a longitudinal (vertical) height (H3) between inner surfaces of the top and bottom surface of the rounded rectangular portion, as illustrated in FIG. 1I. The height (H3) may be from 9.0 mm to 15.0 mm, for example 10.5 mm, 12.3 mm, or 14.1 mm.

In various embodiments, the circular portion has a diameter (H4) defined between the apexes 278, 279. The diameter (H4) may be from 8.0 mm to 17.0 mm, for example 10.0 mm, 14.9 mm, or 16.5 mm. The longitudinal height (H3) of the rounded rectangular portion is less than the diameter (H4) of the circular portion. More specifically, the top apex 278 is disposed above the horizontal region of the rounded rectangular portion, and the bottom apex 279 is disposed below the horizontal region of the rounded rectangular portion. Consequently, the circular portion of the semi-rectangular cross section extends beyond the rounded rectangular portion in a direction parallel to a plane of the semi-rectangular cross section. In some instances, a top region of the circular portion extends beyond the rounded rectangular portion in a first direction parallel to the plane of the semi-rectangular cross section and a bottom region of the circular portion extends beyond the rounded rectangular portion in a second direction parallel to the plane of the semi-rectangular cross section. The second direction may be opposite from the first direction. For e example, a top region of the circular portion may extend above the rounded rectangular portion and a bottom region of the circular portion may extend below the rounded rectangular portion (as shown in FIG. 1I).

In various embodiments, the apexes 278, 279 are part of a first set of curved segments of the semi-rectangular cross section. The first set of curved segments comprising the apexes 278, 279 may have a radius of curvature (R4) that is from 5.1 R to 7.7 R, for example 6.0 R, 6.4 R, or 6.6 R. In various embodiments, the semi-rectangular cross section further comprises a second set of curved segments defined by the convex surface of the four equal circles of radius r (i.e., the turns from the side faces 276, 277 to the top faces 272, 273 and bottom faces 274, 275). The curved segments of the second set of curved segments are located between each of the first top face and the first side face, the first bottom face and the first side face, the second top face and the second side face, and the second bottom face and the second side face. The second set of curved segments may have a radius of curvature (R5) that is from 2.2 R to 3.4 R, for example 2.4 R, 2.8 R, or 3.0 R.

In some embodiments, the top faces 272, 273 and the bottom faces 274, 275 are segments formed tangentially to the convex surface of the four equal circles of radius r at a given point. In certain embodiments, the tangential angle (A3) between the tangential segments of each of the top faces 272, 273 and the bottom faces 274, 275 and a horizontal mid line 280 of the semi-rectangular cross section is an acute angle (i.e., less than 90.0° but greater than 0.0°). In some embodiments, the acute angle is greater than 1.0°. In some embodiments, the acute angle is from 13.0° to 19.6°, for example 16.0°, 16.3°, or 16.6°. The top faces 273, 272 and the top apex 278 define a top region of the circle portion of the semi-rectangular cross section. The bottom faces 275, 274 and the bottom apex 279 define a bottom region of the circle portion of the semi-rectangular cross section. The radius of curvature (R4) for the first set of curved segments comprising the apexes 278, 279 defines a radius of curvature for a top portion and a bottom portion of the circle portion of the semi-rectangular cross section. The radius of curvature (R5) for the second set of curved segments defined by the convex surface of the four equal circles of radius r defines a radius of curvature for the corners of the rounded rectangular portion. The tangential segments of each of the top faces 272, 273 and the bottom faces 274, 275 are configured to join the circular portion with the rounded rectangular portion while maintaining a smooth outer surface for sealing. The tangential angle (A3) maintains the neuromodulation system in a horizontal position within the rounded rectangular portion and maintains the one or more surgical instruments centered along a longitudinal axis of the circular portion.

In various embodiments, the semi-rectangular cross section of a portion of the obturator body 120, the sleeve body 225, the distal opening 227, the proximal opening 229, the distal opening 240, and the proximal opening 245 allow for the obturator assembly 105 and the cannula assembly 107/200 to be used in combination to create a laparoscopic port into a cavity of a body. Moreover, in accordance with some aspects, the sleeve body 225, the distal opening 227, the proximal opening 229, the distal opening 240, and the proximal opening 245 allow for delivery of a neuromodulation system into the cavity and subsequent manipulation, (e.g., visualize, move, modify, or attach tools to), of the neuromodulation system in order to implant the pulse generator in the cavity, position the leads, and attach a neural interface to the target biological structure, without causing trauma to the surrounding structures or the target biological structure. For example, it has been discovered that the use of a semi-rectangular cross section allows for a neuromodulation system to be passed through the cannula assembly 107/200 using the rounded rectangular portion in order to deliver the neuromodulation system into the cavity and separately allows for surgical instruments such as laparoscopes, graspers, scissors, staplers, etc. to be passed through the same cannula assembly 107/200 using the circular portion to manipulate and implant the neuromodulation system within the cavity.

Figure 3A:
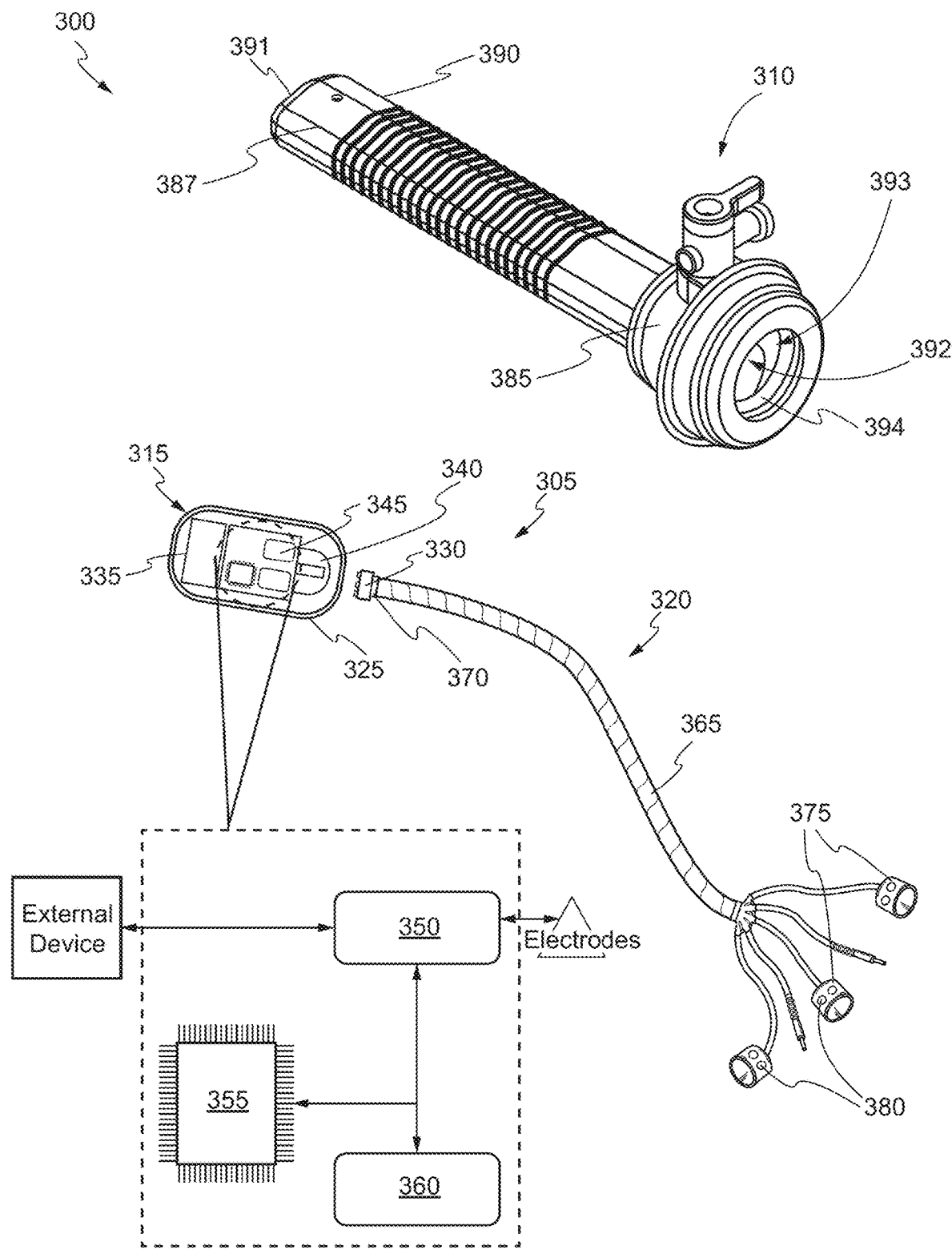
FIGS. 3A-3D show a neuromodulation delivery system in accordance with various embodiments.
Figure 3B:
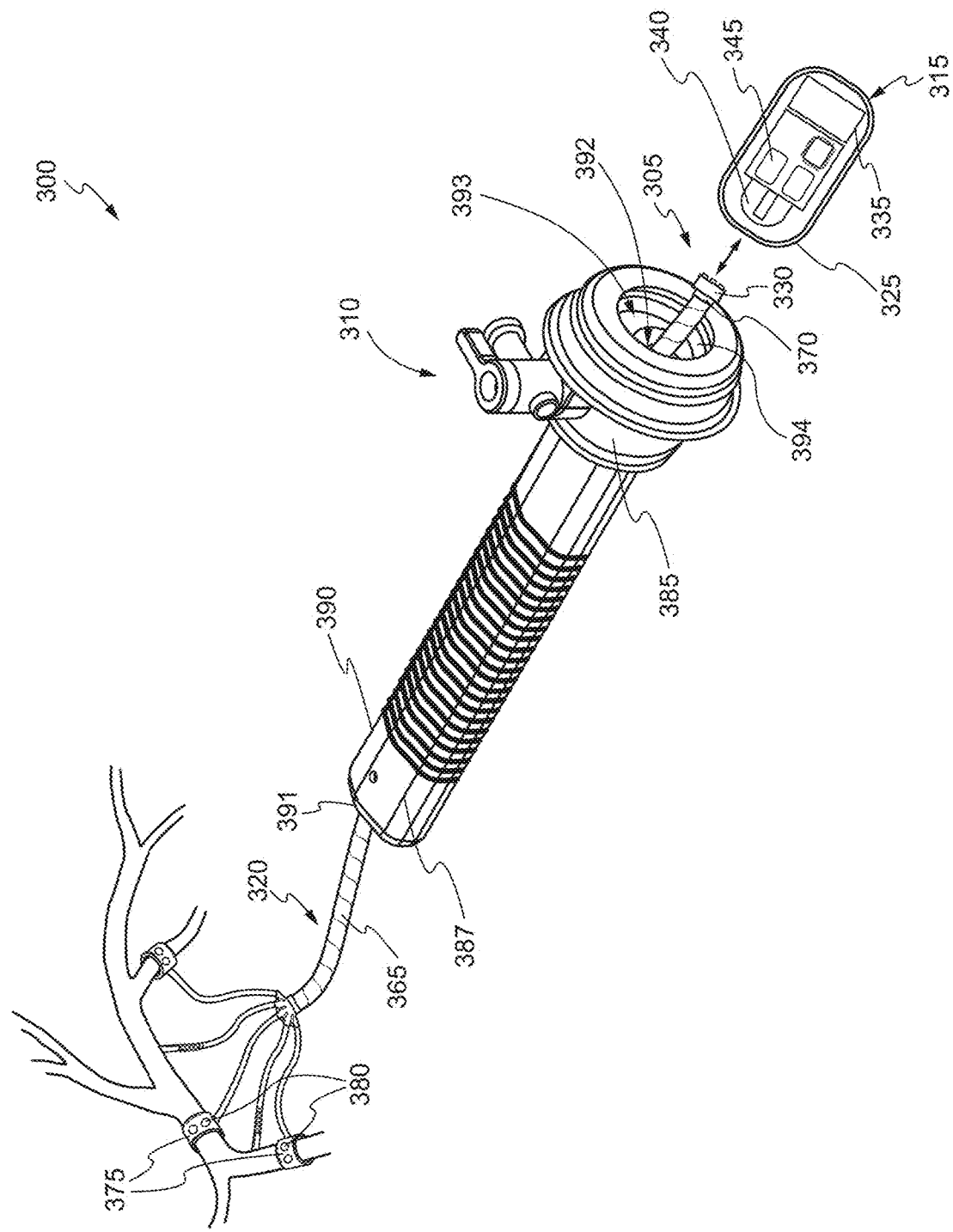
Figure 3C:
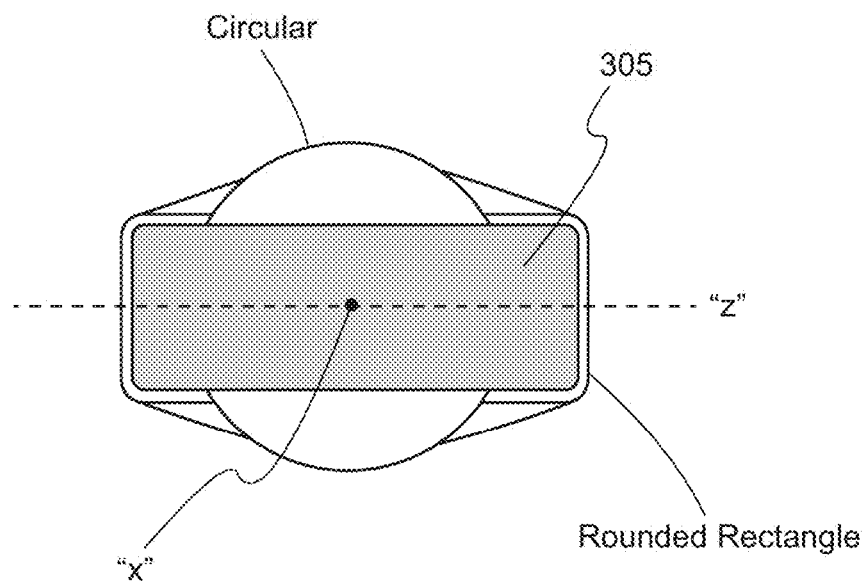

FIGS. 3A-3C show a neuromodulation delivery system 300 for delivering a medical device or system for neuromodulation to the site of the target biological structure in accordance with various aspects. In some embodiments, the neuromodulation delivery system 300 includes two principal components, namely, a neuromodulation system 305 and a trocar or laparoscopic port assembly 310 (e.g., the trocar or laparoscopic port assembly 100 described with respect to FIGS. 1A-1K and 2A-2L.) As shown in FIG. 3A, the neuromodulation system 305 may include an implantable neurostimulator 315 and a lead assembly 320. In certain embodiments, the implantable neurostimulator 315 includes a housing 325, a feedthrough assembly 330, a power source 335, an antenna 340, and an electronics module 345 (e.g., a computing system). The housing 325 may be comprised of materials that are biocompatible such as bioceramics or bioglasses for radio frequency transparency, or metals such as titanium. The size and shape of the housing 325 are selected such that the neurostimulator 315 can be implanted in a less complex and minimally invasive manner, for example, through the trocar or laparoscopic port assembly 310 (see, e.g., FIG. 3B). As such, in various embodiments, the housing 325 has a width of less than 24 mm, for example from 10 mm to 20 mm, a height of less than 15 mm, for example from 5 mm to 13 mm, a length of less than 80 mm, for example from 20 mm to 40 mm, and a cross sectional area of less than 190 mm$^2$, for example from 75 mm$^2$ to 160 mm$^2$.

The feedthrough assembly 330 may be attached to a hole in a surface of the housing 325 such that the housing 325 is hermetically sealed. The feedthrough assembly 330 may include one or more feedthroughs (i.e., electrically conductive elements, pins, wires, tabs, pads, etc.) mounted within and extending through the surface of the housing 325 or a cap from an interior to an exterior of the housing 325. The power source 335 may be within the housing 325 and connected (e.g., electrically connected) to the electronics module 345 to power and operate the components of the electronics module 345. The antenna 340 may be connected (e.g., electrically connected) to the electronics module 345 for wireless communication with external devices via, for example, radiofrequency (RF) telemetry.

In some embodiments, the electronics module 345 is connected (e.g., electrically connected) to interior ends of the feedthrough assembly 330 such that the electronics module 345 is able to apply a signal or electrical current to leads of the lead assembly 320 connected to exterior ends of the feedthrough assembly 330. The electronics module 345 includes discrete and/or integrated electronic circuit components that implement analog and/or digital circuits capable of producing the functions attributed to the neuromodulation devices or systems. In certain embodiments, the electronics module 345 includes software and/or electronic circuit components such as a pulse generator 350 that generates a signal to deliver a voltage, current, optical, or ultrasonic stimulation to a nerve or artery/nerve plexus via electrodes, a controller 355 that determines, senses or records electrical activity and physiological responses via the electrodes and optionally sensors (e.g., a blood pressure sensor), controls stimulation parameters of the pulse generator 350 (e.g., control stimulation parameters based on feedback from the physiological responses) and causes on-demand delivery of the stimulation via the pulse generator 350 and electrodes, and a memory 360 with program instructions operable on by the pulse generator 350 and the controller 355 to perform one or more processes for delivering neurostimulation.

In various embodiments, the lead assembly 320 includes a lead body 365, a lead connector 370, and one or more electrode assemblies 375. In some embodiments, the lead connector 370 is bonding material that bonds conductor material of the lead body 365 to the electronics module 345 of the implantable neurostimulator 315 via the feedthrough assembly 330. The bonding material may be a conductive epoxy or a metallic solder or weld such as platinum. In other embodiments, the lead connector 370 is conductive wire or tab (e.g., a wire or tab formed of copper, silver, or gold) that bonds conductor material of the lead body 365 to the electronics module 345 of the implantable neurostimulator 315. In alternative embodiments, the implantable neurostimulator 315 and the lead body 365 may be designed to connect with one another via a lead connector 370 such as a pin and sleeve connector, snap and lock connector, flexible printed circuit connectors, or other means known to those of ordinary skill in the art.

The lead body 365 may include one or more leads of conductive material and insulator. The one or more leads carry electrical conductors that allow electrical coupling of the electronics module 345 to electrodes 380 of the one or more electrode assemblies 375 via the lead connector 370. In some examples the one or more leads are extruded with a dielectric material such as a polymer having suitable dielectric, flexibility and biocompatibility characteristics. Polyurethane, polycarbonate, silicone, polyethylene, fluoropolymer and/or other medical polymers, copolymers and combinations or blends can be used. In some embodiments, the conductive material for the one or more leads may serve as a strengthening member onto which the body of the lead is extruded. For example, a distal electrode may couple to a centrally located wire on which the body of lead is extruded. The conductive material may be any suitable conductor such as stainless steel, silver, copper or other conductive materials, which may have separate coatings or sheathing for anticorrosive, insulative and/or protective reasons. The conductive material may take various forms including wires, drawn filled tubes, helical coiled conductors, microwires, and/or printed circuits, for example.

FIG. 3A also shows the trocar or laparoscopic port assembly 310 may include a cannula housing 385 and a cannula sleeve 387 extending from the distal end of the cannula housing 385, as described with respect to FIGS. 2A-2L. The semi-rectangular cross section of the sleeve body 390, the distal opening 391 of the sleeve body 390, the proximal opening 392 of the sleeve body 390, the distal opening 393 of the cannula housing 385, and the proximal opening 394 of the cannula housing 385 allow for the trocar or laparoscopic port assembly 310 to be used to create a laparoscopic port into a cavity of a body for the neuromodulation system 305 and surgical instruments (see, e.g., FIG. 3B).

Figure 3D:
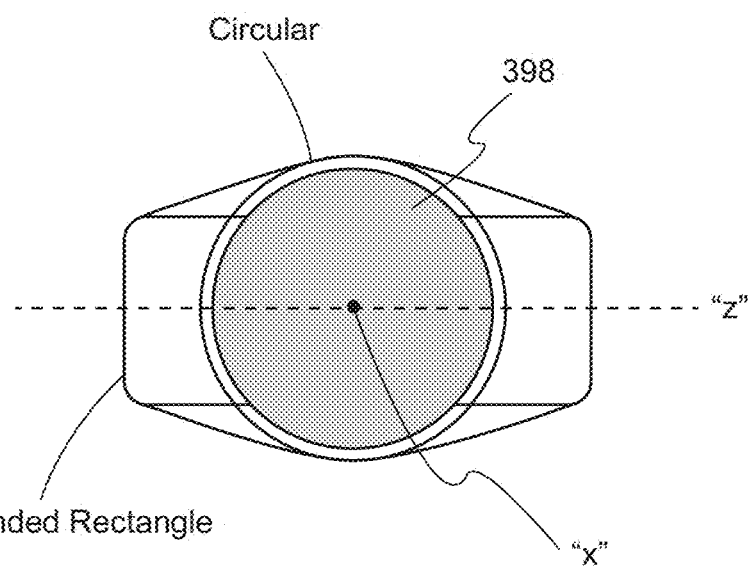

As shown in FIGS. 3C and 3D, the use of the semi-rectangular cross section allows for the neuromodulation system 305 to be passed through the cannula assembly 310 using the rounded rectangular portion in order to deliver the neuromodulation system 305 into the cavity, and separately allows for a surgical instrument 398 such as a laparoscope, grasper, scissor, stapler, etc. to be passed through the cannula assembly 310 using the circular portion to manipulate and implant the neuromodulation system 305 within the cavity. In some embodiments, the dimensions of the semi-rectangular cross section for the trocar or laparoscopic port assembly 310 are specifically configured to maintain the neuromodulation system 305 in a substantial horizontal position ("Z") from the point of insertion at the proximal opening 394 until delivery to the cavity via distal opening 391. Additionally, the dimensions of the semi-rectangular cross section for the trocar or laparoscopic port assembly 310 are specifically configured to maintain the instrument 398 substantially centered along a longitudinal axis ("X") within the trocar or laparoscopic port assembly 310 during manipulation.

For example, in order to fit a neuromodulation system 305 within a housing 325 having a width of about 20 mm, a height of about 10 mm, and a length of about 80 mm, and separately fit a surgical instrument 398 having a diameter of between about 5 mm and about 10 mm, the rounded rectangular portion has a latitudinal (horizontal) width between inner surfaces of the side faces from 20.1 mm to 25 mm and a longitudinal (vertical) height between the top and bottom surface of the rounded rectangular portion from 10.1 mm to 15.0 mm, as illustrated in FIG. 3C. Moreover, in order to maintain the neuromodulation system 305 in a substantial horizontal position and the surgical instrument 398 substantially centered, the radius of curvature (R4) for first set of curved segments comprising the apexes are from 5.1 R to 7.7 R, the radius of curvature (R3)/(R5) for the second set of curved segments comprising the side faces to the top faces and the side faces to the bottom faces is from 2.2 R to 3.4 R, and the tangential angle (A3) between the tangential segments of each of the top faces and bottom faces is an acute angle (i.e., less than 90.0° but greater than 0.0°), for example, greater than 1.0° or from 13.0° to 19.6°. As shown in FIGS. 3C and 3D, the radius of curvatures (R3), (R4), and (R5) accommodate the outer profile of the neuromodulation system 305 and the instrument 398 while maintaining an offset of about 0.25 mm such that the neuromodulation system 305 and the instrument 398 can pass through the trocar or laparoscopic port assembly 310 in an unobstructed manner. The tangential angle (A3) accommodates the outer profile of the neuromodulation system 305 while preventing the neuromodulation system 305 from rotating within the trocar or laparoscopic port assembly 310 to a position that is not substantially horizontal. Additionally, the tangential angle (A3) accommodates the outer profile of the instrument 398 while preventing the instrument 398 from shifting within the trocar or laparoscopic port assembly 310 to a position that is not substantially centered within the trocar or laparoscopic port assembly 310.

Figure 4:
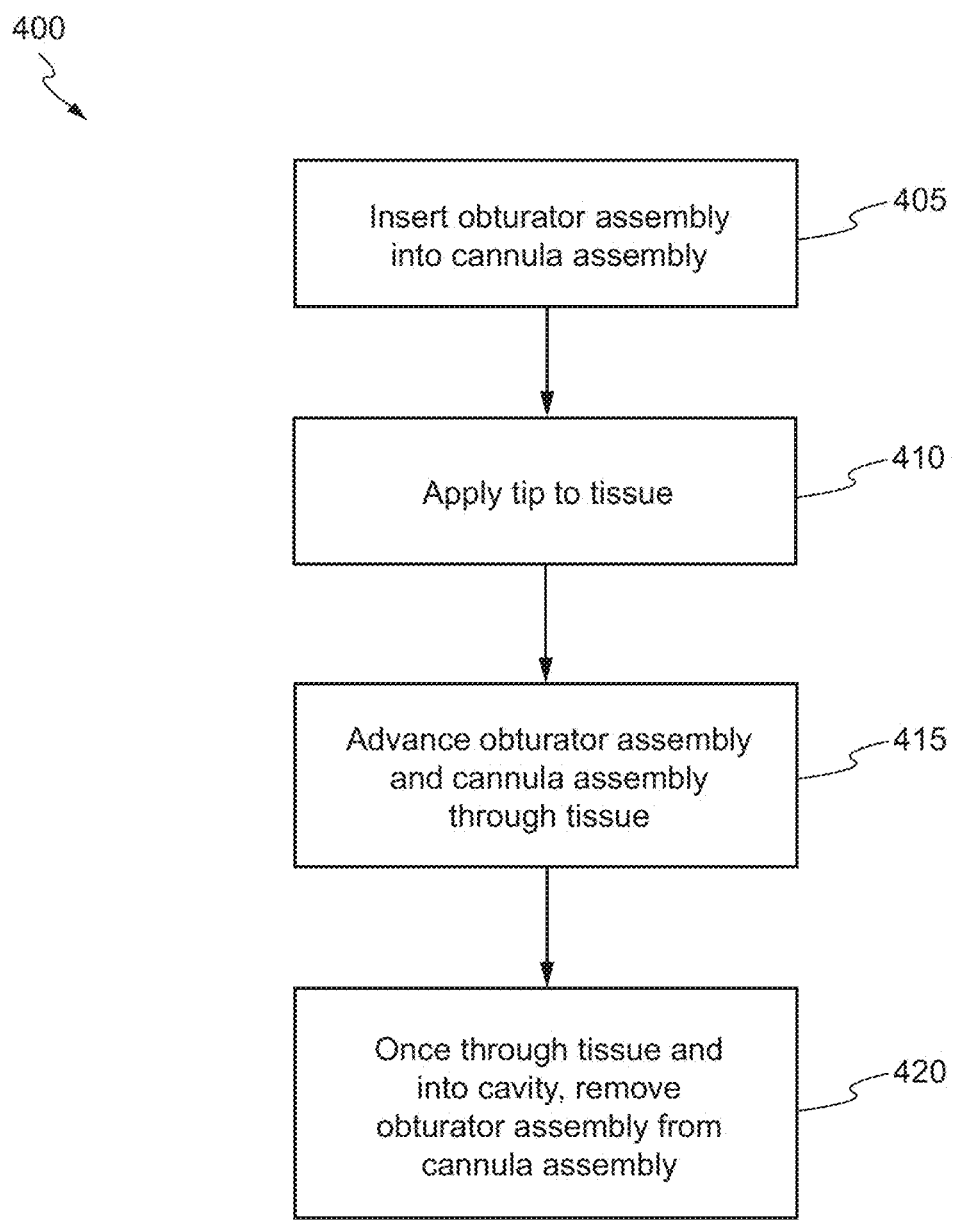
FIGS. 4 and 5 show exemplary flows for providing multimodal therapy in accordance with various embodiments.
Figure 5:
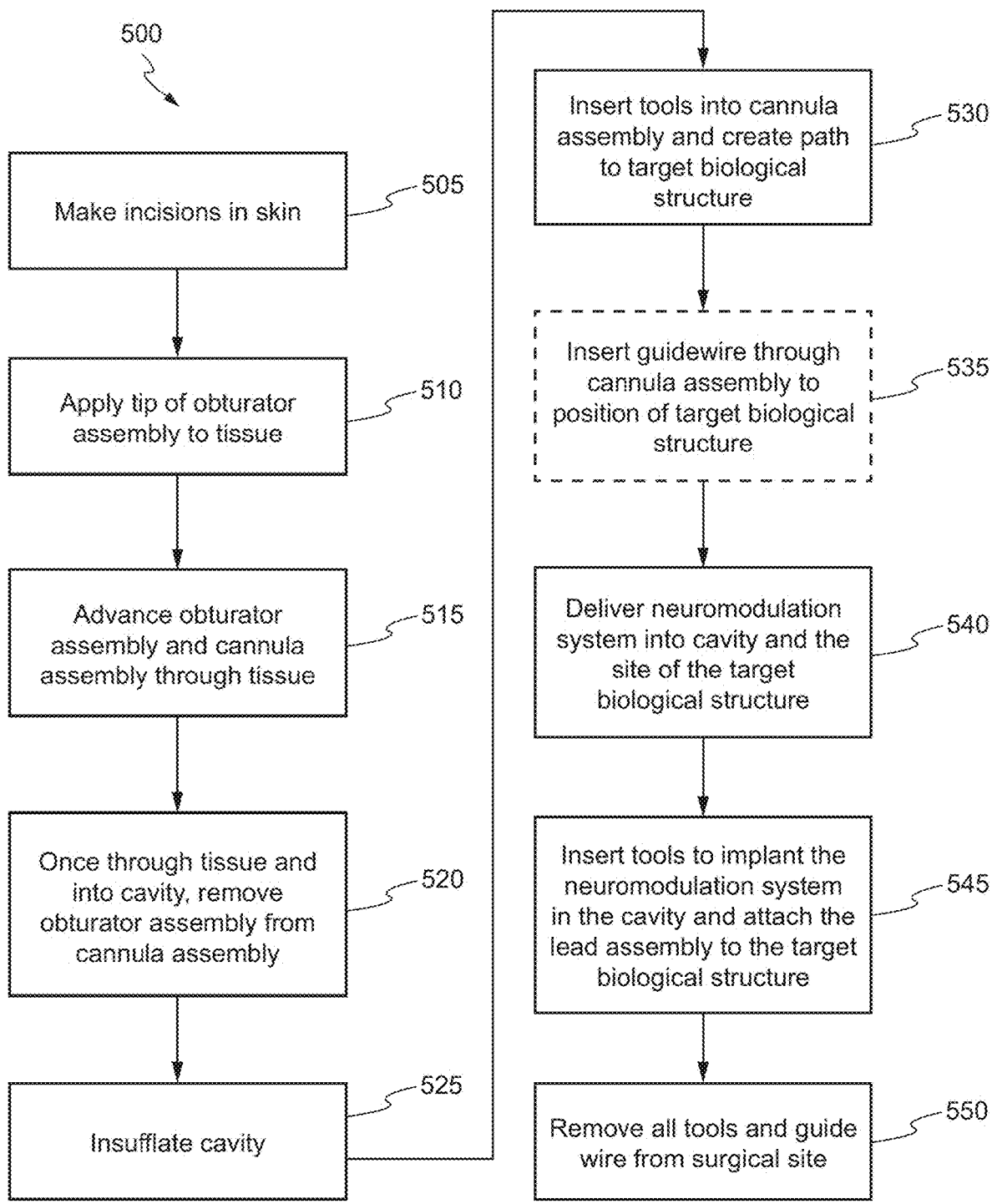

III. Methods for Accessing a Site of a Target Biological Structure and Delivering a Medical Device or System for Neuromodulation to the Site of the Target Biological Structure FIGS. 4 and 5 depict simplified flowcharts depicting processing performed accessing a site of a target biological structure in a patient and delivering a medical device or system for neuromodulation to the site of the target biological structure according to various embodiments. As noted herein, the flowcharts of FIGS. 4 and 5 illustrate the architecture, functionality, and operation of possible implementations of systems, methods, and computer program products according to various embodiments of the present invention. In this regard, each block in the flowchart or block diagrams may represent a module, segment, or portion of code, which comprises one or more executable instructions for implementing the specified logical functions. It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combination of blocks in the block diagrams and/or flowchart illustration, can be implemented manually by a user such as a surgeon or by special purpose hardware-based systems that perform the specified functions or acts, or combinations of special purpose hardware and computer instructions.

FIG. 4 depicts a simplified flowchart 400 illustrating a process used by a user to access a site of a target biological structure in a patient. In some embodiments, the site of the target biological structure is accessed using the trocar or laparoscopic port assembly described with respect to FIGS. 1A-1K, 2A-2L, and 3A-3D. In step 405, an obturator assembly (e.g., the obturator assembly 105 described with respect to FIGS. 1A-1K) is inserted within a cannula assembly (e.g., the cannula assembly 107/200 described with respect to FIGS. 1B and 2A-2L), and advanced to where the obturator housing is approximated with the cannula housing such that a tip of the obturator assembly protrudes from the distal end of the cannula assembly. In various embodiments, the outer wall of the obturator housing is appropriately dimensioned to form a friction fit with annular element of cannula housing or may be coupled to each other by conventional means including bayonet coupling, tongue-groove, etc. At step 410, the obturator tip is applied against tissue such that the arcuate leading surface of the obturator assembly engages the tissue. In various embodiments, the arcuate leading surface may be manipulated to advance within a previously formed incision. At step 415, the obturator assembly and the cannula assembly are advanced through the tissue (e.g., the body wall), which dissects the tissue and causes a trocar or laparoscopic port to be formed through the tissue. In various embodiments, a distally-directed force may be applied to the obturator assembly to cause the advancement of the obturator assembly through the tissue in an atraumatic manner. At step 420, once a portion of the obturator assembly passes through the tissue (e.g., the body wall) into a cavity of the patient (e.g., the abdominal cavity), the obturator assembly is removed from the cannula assembly, which leaves the cannula assembly embedded through the tissue to function as a trocar or laparoscopic port (e.g., a hollow tube) to the cavity, and implantation/surgery may be performed with systems and instruments inserted through cannula assembly.

FIG. 5 depicts a simplified flowchart 500 illustrating a process used to deliver a medical device or system for neuromodulation to the site of the target biological structure. In various embodiments, the method provides access to the target biological structure, (e.g., the splenic plexus), using the trocar or laparoscopic port assembly described with respect to FIGS. 1A-1K, 2A-2L, and 3A-3D. The method provides an atraumatic technique to access the target biological structure and attach an electrode assembly on the target biological structure. In the illustrative embodiments discussed herein, the methods are discussed in the context of accessing a plexus, (e.g., the splenic plexus), and attaching a neuromodulation system to the splenic plexus. However, it should be understood that the methods may be used in any laparoscopic procedure without departing from the spirit and scope of the present invention.

At step 505, one or more incisions are made in the skin of a patient to access a target biological structure underneath the skin. In some embodiments, the one or more incisions may be made near the abdominal region of a patient. In certain embodiments, the one or more incisions may have a diameter in the range from 1 mm to 10 mm, (e.g., from 2 mm to 8 mm or from 4 mm to 6 mm). In some embodiments, the one or more incisions may be enlarged with a medical tool, (e.g., a scalpel), to accommodate a trocar or laparoscopic port assembly (e.g., the trocar or laparoscopic port assembly described with respect to FIGS. 1A-1K, 2A-2L, and 3A-3D) in each of the incisions. At step 510, the obturator tip for a trocar or laparoscopic port assembly is applied against tissue within an incision such that the arcuate leading surface of the obturator assembly engages the tissue. At step 515, the obturator assembly and the cannula assembly are advanced through the tissue (e.g., the body wall), which dissects the tissue and causes a trocar or laparoscopic port to be formed through the tissue. In various embodiments, a distally-directed force may be applied to the obturator assembly to cause the advancement of the obturator assembly and the cannula assembly through the tissue in an atraumatic manner. At step 520, once a portion of the obturator assembly passes through the tissue (e.g., the body wall) into a cavity of the patient (e.g., the abdominal cavity), the obturator assembly is removed from cannula assembly, which leaves the cannula assembly embedded through the tissue to function as a trocar or laparoscopic port to the cavity. As should be understood, multiple trocar or laparoscopic port assemblies may be used such that each of the one or more incisions has a cannula assembly inserted within a respective trocar or laparoscopic port.

At step 525, a volume or cavity underneath the skin is insufflated. The insufflation can include introducing a gas (e.g., $CO_2$ gas). In some embodiments, an insufflation device for delivering a gas is attached to the stop-cock valve of the cannula assembly and the stop-cock switch is operated to enlarge the operative field to access the target biological structure. In some embodiments, when the incision is made in the abdominal cavity of a patient, a needle is inserted through the one or more trocars. The needle may comprise a sharp needle having a lumen. By insufflating the area underneath the skin, the pressure from the gas may retract the anterior abdominal wall exposing the operative field to the target biological structure.

At step 530, one or more surgical instruments are placed through the cannula assembly for creating a pathway to the target biological structure. In some embodiments, after insufflation, the one or more surgical instruments such as laparoscopic tools may be used for manual dissection of biological structures to create a pathway to the target biological structure. For example, graspers can be inserted through one or more of cannula assemblies to move or dissect biological structures along natural tissue planes to provide a pathway to access the target biological structure. In other embodiments, graspers, dissectors, scissors, retractors, etc., are placed through the one or more of cannula assemblies for manipulations of the operative field or target biological structure by the user, (e.g., a surgeon). Once the pathway is created, the one or more surgical instruments may be removed from the cannula assembly. As described herein, the use of the semi-rectangular cross section allows for the one or more surgical instruments to be passed through the cannula assembly using the circular portion and manipulated to create the pathway to the target biological structure.

Optionally at step 535, a guidewire is inserted through the cannula assembly to a position of the target biological structure. In various embodiments, the guidewire is inserted through the cannula assembly to provide a track for the neuromodulation system and surgical instruments to access the target biological structure. For example, the guidewire may be inserted through the cannula assembly towards the exterior surface of the target biological structure. In some embodiments, after manual dissection with the laparoscopic tools, the guidewire is threaded through the pathway created by the dissection.

At step 540, a neuromodulation system is delivered through the cannula assembly into the cavity and the site of the target biological structure. In various embodiments, after the pathway is created to the target biological structure (and optionally the guidewire is inserted), the implantable neurostimulator and the lead assembly are fed through the cannula assembly into the cavity. In some embodiments, the implantable neurostimulator is introduced over the guidewire and guided through the cannula assembly and delivered into the cavity. Additionally or alternatively, the lead assembly may be introduced over the guidewire and guided through the cannula assembly into the cavity and delivered to the site of the target biological structure. The implantable neurostimulator and the lead assembly may be delivered through the cannula assembly at the same time or separate from one another depending on the circumstances and type of neuromodulation system being used for therapy. For example, in an instance where the lead assembly is removable from the implantable neurostimulator, the implantable neurostimulator may be delivered and implanted in the cavity, and subsequently the lead assembly may be delivered, attached to the target biological structure and electrically connected to the implantable neurostimulator.

At step 545, one or more surgical instruments are placed through the cannula assembly for implanting the implantable neurostimulator in the cavity and attaching the lead assembly to the target biological structure. In some embodiments, after being delivered through the cannula assembly, one or more surgical instruments such as laparoscopic tools may be used for manual manipulation of the implantable neurostimulator and tissue within the cavity to implant the implantable neurostimulator within the cavity. For example, graspers can be inserted through one or more of cannula assemblies to move the implantable neurostimulator and a stapler or suturing device may be used to attach the implantable neurostimulator to a wall of the cavity. In some embodiments, graspers, dissectors, scissors, retractors, etc., are also placed through the one or more of cannula assemblies for manipulations of the operative field, tissue, or target biological structure by the user, (e.g., a surgeon). As described herein, the use of the semi-rectangular cross section allows for the one or more surgical instruments to be passed through the cannula assembly using the circular portion and manipulated to implant the implantable neurostimulator.

In some embodiments, after being delivered through the cannula assembly, one or more surgical instruments such as laparoscopic tools may be used for manual manipulation of the lead assembly and the target biological structure to attach the lead assembly to the target biological structure. For example, graspers can be inserted through one or more of cannula assemblies to move the lead assembly and a deployment device may be used to attach an electrode structure to the target biological structure. In some embodiments, graspers, dissectors, scissors, retractors, etc., are also placed through the one or more of cannula assemblies for manipulations of the operative field, tissue, or target biological structure by the user, (e.g., a surgeon). As described herein, the use of the semi-rectangular cross section allows for the one or more surgical instruments to be passed through the cannula assembly using the circular portion and manipulated to attach the electrode structure to the target biological structure.

In various embodiments, one or more surgical instruments such as laparoscopic tools may be used to deliver and implant/attach the implantable neurostimulator and/or the lead assembly. For example, an electrode deployment tool may be used to deliver the electrodes of the lead assembly to the target biological structure. The electrode deployment tool may include an interior volume and an electrode structure (e.g., an electrode cuff) positioned within the interior volume. The electrode structure in the electrode deployment tool may be deployed such that electrode structure moves from within the interior volume to an extended position near the target biological structure. As described herein, the use of the semi-rectangular cross section allows for the implantable neurostimulator and/or the lead assembly to be passed through the cannula assembly using the rounded rectangular portion and for one or more surgical instruments to be passed through the cannula assembly using the circular portion.

At step 550, each of the cannula assemblies and one or more surgical instruments (and optionally the guidewire) used in the process are removed from the surgical site. Specifically, the surgical instruments such as laparoscopic tools and guidewire are each removed via one of the cannula assemblies, and the cannula assemblies are then removed from the trocar or laparoscopic ports to the cavity. In some embodiments, the trocar or laparoscopic ports are closed using sutures, staples, or similar closing devices. The implantable neurostimulator remains implanted within the cavity and the lead assembly remains attached to the target biological structure.

While the invention has been described in detail, modifications within the spirit and scope of the invention will be readily apparent to the skilled artisan. It should be understood that aspects of the invention and portions of various embodiments and various features recited above and/or in the appended claims may be combined or interchanged either in whole or in part. In the foregoing descriptions of the various embodiments, those embodiments which refer to another embodiment may be appropriately combined with other embodiments as will be appreciated by the skilled artisan. Furthermore, the skilled artisan will appreciate that the foregoing description is by way of example only, and is not intended to limit the invention.

What is claimed is:

1. A cannula sleeve in a cannula assembly comprising:
   a sleeve body comprising a proximal end and a distal end, the distal end having an opening; and
   a hub attached to the proximal end of the sleeve body to be connected to the sleeve body, the hub configured to fit with a cannula housing, wherein the hub matches a size and shape of a portion of the cannula housing for securing the cannula sleeve to the cannula housing, wherein the sleeve body comprises:

a first side face connecting a first set of rounded corners;

a second side face opposing the first side face, the second side face connecting a second set of rounded corners, wherein the first set of rounded corners and the second set of rounded corners each comprise an upper rounded corner and a lower rounded corner;

a top apex extending from the upper rounded corners of the first set of rounded corners and the second set of rounded corners, wherein the top apex is rounded in shape and comprises:

a first top face extending from the upper rounded corner of the first set of rounded corners to the top apex; and a second top face extending from the upper rounded corner of the second set of rounded corners to the top apex; and a bottom apex extending from the lower rounded corners of the first set of rounded corners and the second set of rounded corners, wherein the bottom apex is rounded in shape;

wherein the first side face and the second side face are parallel; and wherein the first top face and the second top face are flat.

2. The cannula sleeve of claim 1, wherein the bottom apex comprises:

a first bottom face extending from the lower rounded corner of the first set of rounded corners to the bottom apex; and a second bottom face extending from the lower rounded corner of the second set of rounded corners to the bottom apex.

3. The cannula sleeve of claim 2, wherein the first top face and the second bottom face are parallel.

4. The cannula sleeve of claim 2, wherein the second top face and the first bottom face are parallel.

5. The cannula sleeve of claim 1, wherein longitudinal height of the first set of rounded corners and the second set of rounded corners is less than a distance between the top apex and the bottom apex.

6. The cannula sleeve of claim 1, wherein a cross section of the sleeve body from the proximal end to the distal end, along a longitudinal axis of the sleeve body, has a consistent shape throughout.

* * * * *